US012656332B2

(12) United States Patent
Kay et al.

(10) Patent No.: US 12,656,332 B2
(45) Date of Patent: Jun. 16, 2026

(54) SECURE ANALYSIS SYSTEM

(71) Applicant: K2R2 LLC, Camarillo, CA (US)

(72) Inventors: Robert L Kay, Thousand Oaks, CA (US); Graham Ross, Oceanside, CA (US); Stephanie Kay, Thousand Oaks, CA (US)

(73) Assignee: K2R2 LLC, Camarillo, CA (US)

( * ) Notice: Subject to any disclaimer, the term of this patent is extended or adjusted under 35 U.S.C. 154(b) by 1094 days.

(21) Appl. No.: 17/724,468

(22) Filed: Apr. 19, 2022

(65) Prior Publication Data

US 2022/0244236 A1 Aug. 4, 2022

Related U.S. Application Data

(63) Continuation-in-part of application No. 17/592,721, filed on Feb. 4, 2022, now Pat. No. 11,860,103, which is a continuation-in-part of application No. 17/395,814, filed on Aug. 6, 2021, now Pat. No. 11,619,588.

(60) Provisional application No. 63/105,763, filed on Oct. 26, 2020.

(51) Int. Cl.
 *G06F 21/60* (2013.01)
 *G01N 33/487* (2006.01)
 *G06F 21/62* (2013.01)

(52) U.S. Cl.
 CPC . *G01N 33/48771* (2013.01); *G01N 33/48778* (2013.01); *G06F 21/602* (2013.01); *G06F 21/6227* (2013.01)

(58) Field of Classification Search
 CPC ..................................................... G06F 21/602
 See application file for complete search history.

(56) References Cited

U.S. PATENT DOCUMENTS

| 7,162,035 | B1 * | 1/2007 | Durst | .................... | G06F 21/602 |
| | | | | | 380/54 |
| 2006/0190202 | A1 * | 8/2006 | Ramsdale | ........... | H04L 41/0806 |
| | | | | | 702/77 |
| 2015/0161413 | A1 * | 6/2015 | Calem | ................. | G06F 21/6245 |
| | | | | | 705/51 |
| 2020/0136938 | A1 * | 4/2020 | Atkinson | .............. | H04L 9/3066 |

* cited by examiner

*Primary Examiner* — Simon P Kanaan

(57) ABSTRACT

A secure analysis system for analyzing a sample is disclosed. The system includes an analyzer configured to create a measurement of the sample, create a data record of the measurement, encrypt the data record to form an encrypted data file, and provide the encrypted data file. The system also includes a server communicatively coupled to the analyzer and configured to receive the encrypted data file, store the encrypted data file, retrieve at least one of an encrypted algorithm, an encrypted parameter, and a portion of an encrypted library. The server is also configured to retrieve an encryption key, decrypt at least one of the data file, the algorithm, the parameter, and the library portion using the key, analyze the measurement, and provide a result.

8 Claims, 16 Drawing Sheets

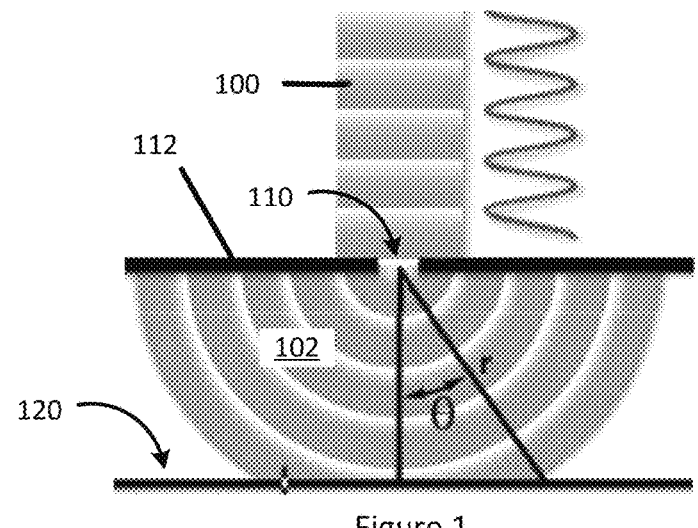
Figure 1
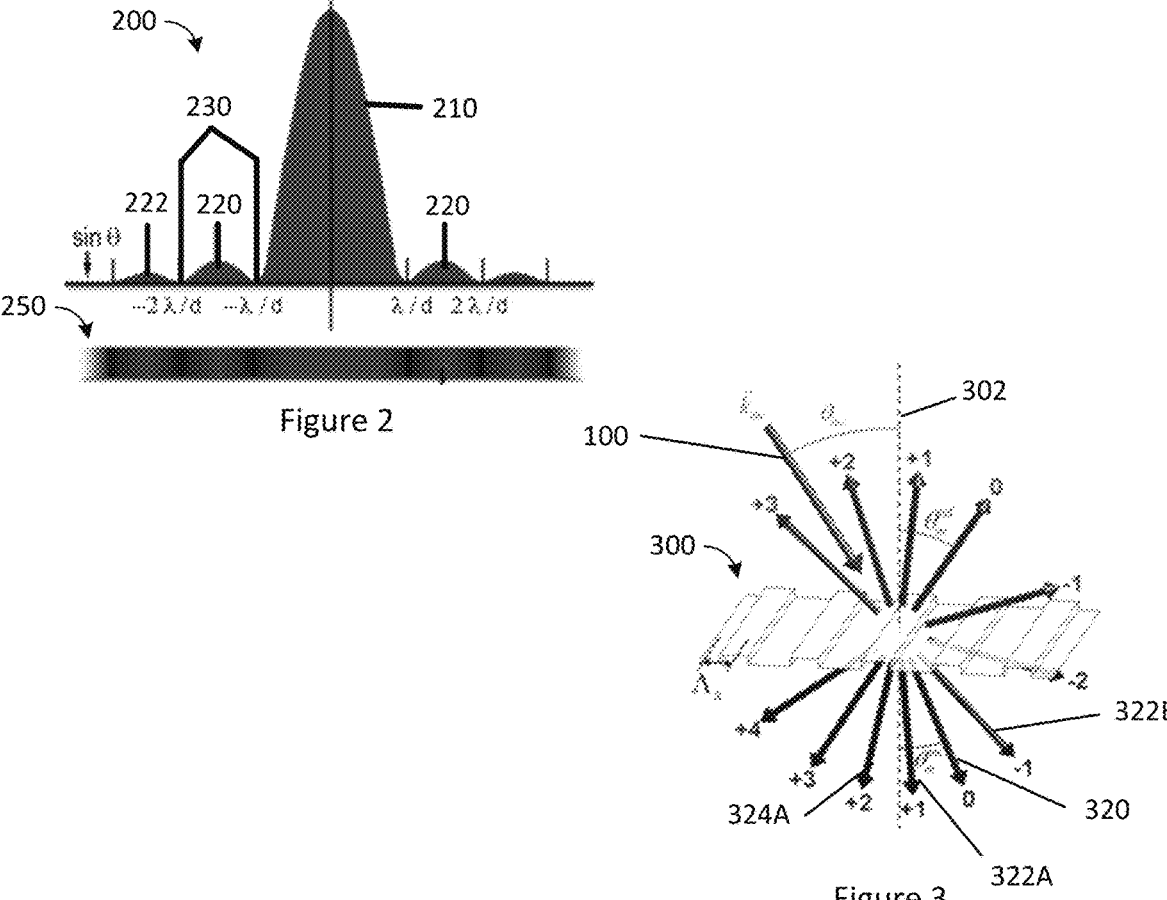
Figure 2
Figure 3

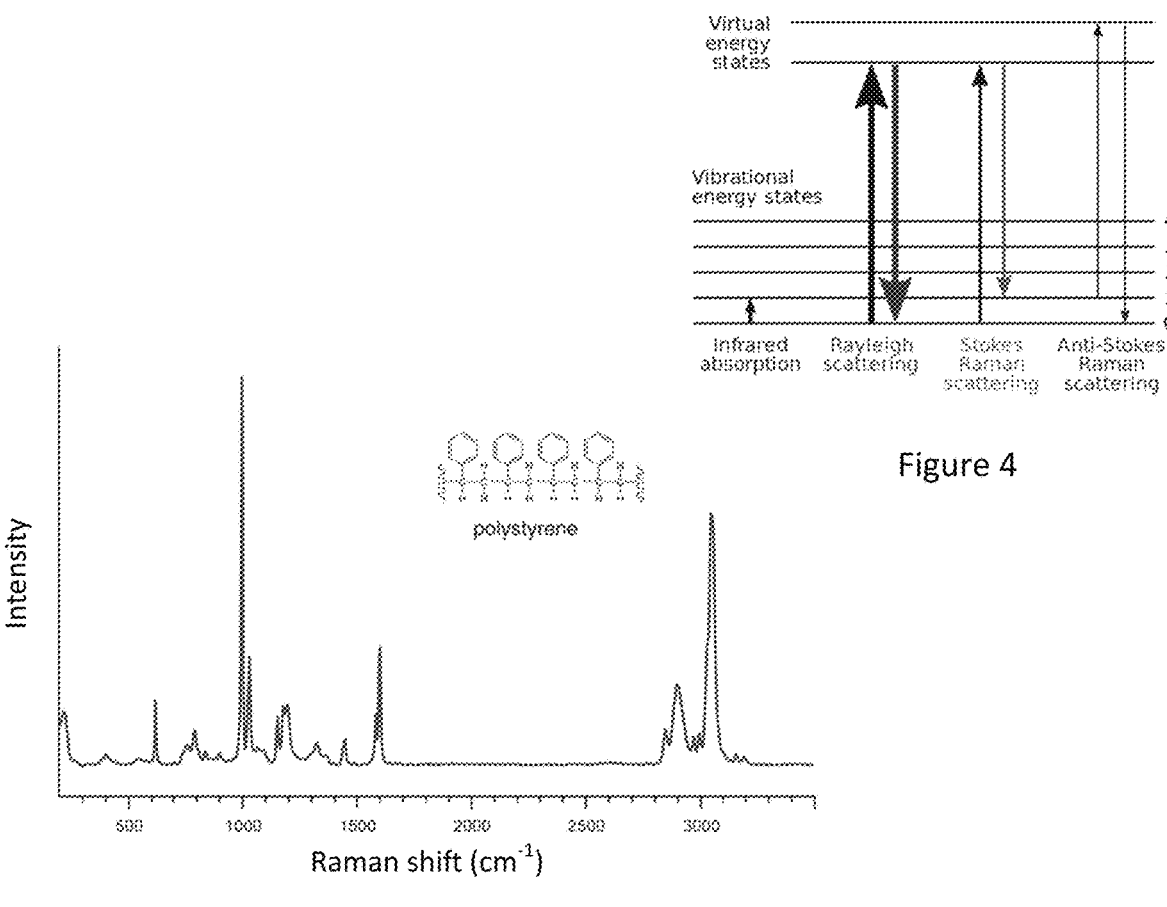
Figure 4
Figure 5
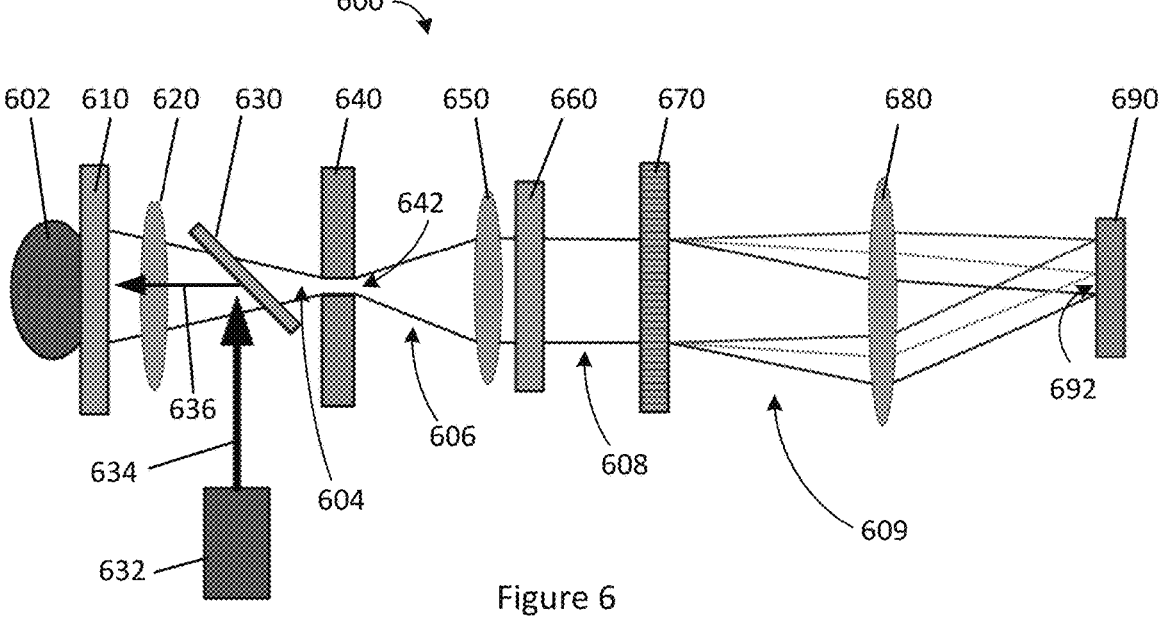
Figure 6

700

HOLDER 710

714   LID

SAMPLE

720   SPECIMEN PLATE

722   SAMPLE LENS ARRAY

724   SLIT ARRAY

726 COLLIMATING LENS ARRAY

712

782

702

770 POWER SOURCE

780 LIGHT SOURCE

730 GRATING

732 FINAL FOCUS LENS

740 DETECTOR

754 USER INTERFACE

750 PROCESSOR

752 COMM MODULE

760 MEMORY

790 SERVER

756 GPS MODULE (CBD)

(THC)

1800

1500     SAMPLE HOLDER

1530     LATCH

1540     IDENTIFIER

1700
SAMPLE CAPTURE DEVICE

1732
SENSOR

1734
SCANNER

1736
CAMERA

1730
PROCESSOR

1712
USER INTERFACE

1750
SERVER

1742
COMM MODULE

1738     GPS
MODULE

1740
MEMORY

SECURE ANALYSIS SYSTEM

CROSS-REFERENCE TO RELATED APPLICATIONS

This application claims priority to U.S. application Ser. No. 17/592,721 filed on Feb. 4, 2022 that claims priority to U.S. application Ser. No. 17/395,814 filed on Aug. 6, 2021 that claims priority U.S. provisional application 63/105,763 filed Oct. 26, 2020, all of which are incorporated herein by reference in their entireties.

STATEMENT REGARDING FEDERALLY SPONSORED RESEARCH OR DEVELOPMENT

Not applicable.

BACKGROUND

Field

The present invention generally relates to identification and handling of a sample of a material and information related to the sample.

Description of the Related Art

Raman spectroscopy, named after Indian physicist C. V. Raman, is a spectroscopic technique used to identify materials. A source of monochromatic light illuminates a sample. The photons of the source light excite the molecules of the sample, which then emit photons that will be at a higher or lower energy level, compared to the incident photons, depending on the vibrational modes of the molecules of the sample. Every molecule has a characteristic "fingerprint" based on its structure. Comparison of the results generated by a sample to a library of material fingerprints enables the determination of the materials in the sample.

Conventional Raman spectrometers suffer from a number of drawbacks including a limited Field of View (FOV), a high numerical aperture (NA) that inherently results in a shallow Depth of Field (DOF), and a significant loss of signal due to the use of a single narrow slit. The limited FOV is the result of using a microscope objective as the primary light gathering component. The optical elements of a conventional Raman spectrometer are designed to observe only a small area of the sample, which then requires a scanning mechanism to gather sample observations from multiple points of samples. The optics commonly implement a high NA to maximize the collection of light from a small sample point. A conventional Raman spectrometer uses a single slit in the optical path and the spectral resolution of the spectrometer is inversely related to the width of the slit; i.e., higher spectral resolution requires a narrower slit that inherently causes a reduction in optical signal strength.

Maintaining the integrity of a sample of material when the sample is handled by multiple people and transferred between locations and organizations is a long-standing challenge. Many organizations have strict chain-of-custody procedures to ensure that samples are handled only by authorized individuals. Conventional tamper-evident containers provide some assurance as to whether the container has been opened and reclosed if, and only if, appropriate records are also maintained. For example, if a serialized tie wrap is used to secure a container in a closed configuration, it is necessary to create a record of the original serial number and manually check the current serial number against the record at each step of handling, otherwise a new serialized tie wrap can be installed after the container is opened and re-closed.

SUMMARY

In certain embodiments, it is desirable to provide a robust, compact Raman spectrometer that utilizes a single-use tamper-evident sample holder and creates a linked set of artifacts that provides chain-of-custody evidence from a physical material sample to an analysis result.

A secure analysis system for analyzing a sample is disclosed. The system includes an analyzer configured to create a measurement of the sample, create a data record of the measurement, encrypt the data record to form an encrypted data file, and provide the encrypted data file. The system also includes a server communicatively coupled to the analyzer and configured to receive the encrypted data file, store the encrypted data file, retrieve at least one of an encrypted algorithm, an encrypted parameter, and a portion of an encrypted library. The server is also configured to retrieve an encryption key, decrypt at least one of the data file, the algorithm, the parameter, and the library portion using the key, analyze the measurement, and provide a result.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 1 illustrates diffraction at a slit, according to certain aspects of the present disclosure.

FIG. 2 depicts the intensity distribution of diffracted light, according to certain aspects of the present disclosure.

FIG. 3 depicts the refractive and reflective scattering of modes of an incident beam of monochromatic light, according to certain aspects of the present disclosure.

FIG. 4 illustrates Rayleigh scattering, according to certain aspects of the present disclosure.

FIG. 5 illustrates an example Raman spectrum, according to certain aspects of the present disclosure.

FIG. 6 depicts a schematic representative of a conventional Raman spectrometer, according to certain aspects of the present disclosure.

DETAILED DESCRIPTION

Figure 7:
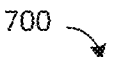
FIG. 7 depicts a block diagram of an exemplary apparatus, according to certain aspects of the present disclosure.

The following description discloses embodiments of a Raman spectrometer that is particularly suited to be carried into the field for use.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form to avoid obscuring the concepts of the subject technology. Like, or substantially similar, components are labeled with identical element numbers for ease of understanding.

As used within this disclosure, the term "light" means electromagnetic energy having a wavelength within the range of 10 nanometers (nm) to 1 millimeter (mm). In certain embodiments, this range is preferably 300-1100 nm. In certain embodiments, this range is preferably 700-1100 nm. In certain embodiments, this range is preferably 10-400 nm (ultraviolet). In certain embodiments, this range is preferably 400-700 nm (visible). In certain embodiments, this range is preferably 700 nm to 1 mm (infrared).

As used within this disclosure, the terms "frequency" (f) and "wavelength" ($\lambda$) should be considered interchangeable in characterizing a beam of light unless explicitly stated otherwise, as they are related by the equation $\lambda = c/f$, wherein "c" is the speed of light, and a value of either parameter is uniquely associated with a respective value of the other parameter. Furthermore, the terms "wavelength" and "wave number" should be considered interchangeable in characterizing a spectral response unless explicitly stated otherwise, as they are inversely related to each other and a value of either parameter is uniquely associated with a respective value of the other parameter.

FIG. 1 illustrates diffraction of a coherent monochromatic light beam 100 at a slit 110 in a plate 112, according to certain aspects of the present disclosure. The white lines in the incident beam 100 represent the "valleys" of the sinusoidal wave of the light, shown to the right for reference. The light that passes through the slit 110 is diffracted, also referred to as "scattered," with the diffracted light 102 propagating as a spherical wave toward a surface 120 as seen in FIG. 1.

FIG. 2 depicts the intensity distribution 200 of diffracted light 102 on surface 120, according to certain aspects of the present disclosure. The central peak 210 is centered under the incident beam 100 and flanked on both sides by secondary lobes (maxima) 220 and dark lines (minima) 230, with the intensity of each succeeding lobe 222 decreasing as the lateral distance from the center increases. The pattern 250 formed on the surface 120 is governed by equation 1:

$$\sin(\theta_1) = 1.22(\lambda/d) \qquad \text{Equation 1}$$

wherein:

$\theta_1$ is the angular position of the first order diffraction minima (the first dark ring)

$\lambda$ is the wavelength of the incident light d is the width of the slit

FIG. 3 depicts the refractive and reflective scattering of modes of an incident beam of monochromatic light, according to certain aspects of the present disclosure. A beam 100 of coherent light strikes the grating 300 at an angle $\theta_{inc}$ relative to an axis 302 that is perpendicular to the plane of the grating 300. A portion of the incident beam 100 is transmissively diffracted into various modes at various angles $$\theta_m^{trn}$$

relative to the incident beam 100, wherein "M" is the mode number. For example, beam 320 is the $0^{th}$-order mode (primary) transmitted mode, beams 322A, 322B are the $1^{st}$-order transmitted modes, and beams 324A, 324B are the $2^{nd}$-order transmitted modes. The $0^{th}$-order mode is at an angle $$\theta_0^{trn}$$

while the $1^{st}$-order modes 322A, 322B are at $$\pm\theta_1^{trn}$$

relative to beam 100.

The angles $$\theta_m^{trn}$$

are dependent upon the frequency of the incident light, the mode order, the geometry, and the index of refraction of the material of the grating 300 as shown in Equation 2. This equation presumes air on both sides of the grating 300.

$$\sin \theta_m = \sin \theta_{inc} - m\frac{\lambda}{\Lambda} \qquad \text{Equation 2}$$

wherein:

$\lambda$ is the wavelength of the incident light $\Lambda$ is the spacing of the lines of the grating m is the order of the refracted ray $\theta$ is the angle from perpendicular to the grating, the subscript "inc" indicates the incident ray and the subscript "m" indicates the $m^{th}$ refracted ray A portion of the incident beam 100 may be reflectively diffracted into various modes at various angles $$\theta_m^{ref}$$

relative to axis 302.

FIG. 4 illustrates Rayleigh scattering, according to certain aspects of the present disclosure. Raman spectroscopy relies upon inelastic scattering of photons. An incident beam of monochromatic light introduces energy into the molecules of a sample material and excites the system. The material emits the absorbed energy at frequencies associated with the various energy states of its molecules. The shift in energy gives information about the vibrational modes in the system.

FIG. 5 illustrates an example Raman spectrum, according to certain aspects of the present disclosure. The light emitted by a material is plotted as intensity vs. frequency shift relative to the frequency of the source light, referred to as the "Raman shift," traditionally measured in a unit called the wavenumber, which is the number of waves per cm ($cm^{-1}$). The spikes of the plot are associated with vibrational modes of chemical bonds in one of the component materials. These spikes are referred to as "Raman bands" and the frequency and relative intensities of the bands allow us to identify the material by comparison of their spectral "signature" with a library of reference signatures of known materials. Heavy atoms and weak bonds have low Raman shifts. Light atoms and strong bonds have high Raman shifts.

The plot of FIG. 5 is the Raman spectrum of polystyrene. The high frequency carbon-hydrogen (C—H) bonds have a resonant frequency that creates the Raman band at about $3000 \ cm^{-1}$. The carbon-carbon (C—C) bonds create the small Raman band at around $800 \ cm^{-1}$. The C—H vibrations have a higher frequency than the C—C vibrations because hydrogen is lighter than carbon. The vibrations of a complex molecule partly consist of many simple diatomic vibrations while also showing the vibrational modes of larger groups of atoms, such as the expanding/contracting "breathing mode" of the aromatic carbon rings in polystyrene that appears at $1000 \ cm^{-1}$.

FIG. 6 depicts a schematic representative of a conventional Raman spectrometer 600, according to certain aspects of the present disclosure. A sample 602 to be characterized is placed against a surface of a sample holder 610. A partially reflective mirror 630 deflects a portion of beam of source light 634 emitted by a light source 632 to travel toward the sample 602 as illumination beam 636. The scattered light emitted by the sample 602 passes through the sample holder 610 and the sample lens 620 to the mirror 630, where a portion 604 of the scattered light continues through a spatial filter, e.g., a slit, 642. The sample lens 310 focuses the light 604 on the spatial filter 642. The light 606 that has passed through the spatial filter 642 is formed into a unidirectional beam 608 by the collimating lens 650. An excitation filter 660 blocks the transmission of the light from source 632. The beam of filtered light 608 strikes the transmissive diffraction grating 670. The diffracted light 609 coming out of the grating 670 is focused by the final focus lens 680 onto surface 692 of a detector 690, which may be a charge-coupled device (CCD) sensor or camera.

FIG. 7 depicts a block diagram 700 of an exemplary Raman spectrometer, according to certain aspects of the present disclosure. An instrument body 702 is configured to accept a holder 710 that has a compartment 712 configured to accept a sample of a material. In certain embodiments, the holder 710 includes a specimen plate 720, a sample lens array 722, a slit array 724, and a collimating lens array 726. In certain embodiments, the specimen plate forms a portion of the compartment 712.

In certain embodiments, the holder 710 comprises a lid 714 configured to selectably close over the accepted sample and permanently prevent removal of the sample from the holder compartment 712. In certain embodiments, closure of the lid 714 is a non-reversable event wherein the lid 714 cannot be opened again without damage to the lid 714 or holder 710, i.e., evidence of tampering. This feature makes the holder 710 into a tamper-evident sample container that can be archived for later retrieval and re-examination. In certain embodiments, the lid 714 is hingedly attached to the body of the holder 710.

The instrument body 702 is coupled to a transmissive grating 730, a focusing lens 732, and a detector 740. The detector 740 is communicatively coupled to a processor 750 and configured to provide information about the Raman spectrum of this sample, i.e., the sample signature, to the processor 750. The processor 750 can store the sample signature and associated data, e.g., a date, a sample ID, a location such as where the sample was collected, a field designator, a user name, etc., in the memory 760. The processor 750 is coupled to a comm module 752 that is communicatively coupled to a server 790 that may be at a remote location or implemented as a virtual device on a "cloud" server. In certain embodiments, the server 790 is implemented as a software service. The body 702 is also coupled to a user interface 754, for example a color graphics display with an overlaid touchscreen. The body 702 is also coupled to a power supply 770 that provides power to all of the electronic components of the apparatus and, in certain embodiments, received information from one of more of the components. In certain embodiments, the body 702 is also coupled to a GPS module 756 that provides location information to the processor 750.

Light 782 from the light source 780 is guided to the sample, which is shown as contained in compartment 712 having a lid 714 in this example. The sample is stimulated by the light 782 to emit light, a portion of which passes through the sample plate 720, the sample lens array 722, the slit array 724, and the collimating lens array 726 to the grating 730. The light is refracted by the grating 726 and a portion of the refracted light passes through the final focus lens 732 to the detector 740.

Detector 740 creates data that is provided to the processor 750. The processor 850 is communicatively coupled a memory 760 via a bidirectional path. In certain embodiments, the memory 760 contains instructions that, when transferred to the processor 750 and executed by the processor 750, cause the processor 750 to receive the data from the detector 740, compare the received data with a portion of one or more reference files, and determine an attribute of the sample.

In certain embodiments, memory 760 also contains the one or more reference files that are respectively associated with one or more materials and the instructions comprise instructions to transfer a portion of the files to the processor 750. In certain embodiments, the one of more reference files are stored on the server 790 that is communicatively connected to the processor 750 through the comm module 752, for example over a wired and/or wireless network.

In certain embodiments, the light source 780 emitting light at a determined frequency. In certain embodiments, the frequency is in the infrared band. In certain embodiments, the frequency is in the visible band. In certain embodiments, the frequency is in the ultraviolet band. In certain embodiments, the light source 780 comprises an optical filter (not shown in FIG. 7) that passes light only in a selected band having a frequency bandwidth. In certain embodiments, the source 780 emits light in a band having a bandwidth that is less than or equal to 5 nm. In certain embodiments, the source 780 emits light in a band having a bandwidth that is less than or equal to 2 nm. In certain embodiments, the light source 780 comprises a plurality of sources each emitting light at a different frequency.

Figure 8:
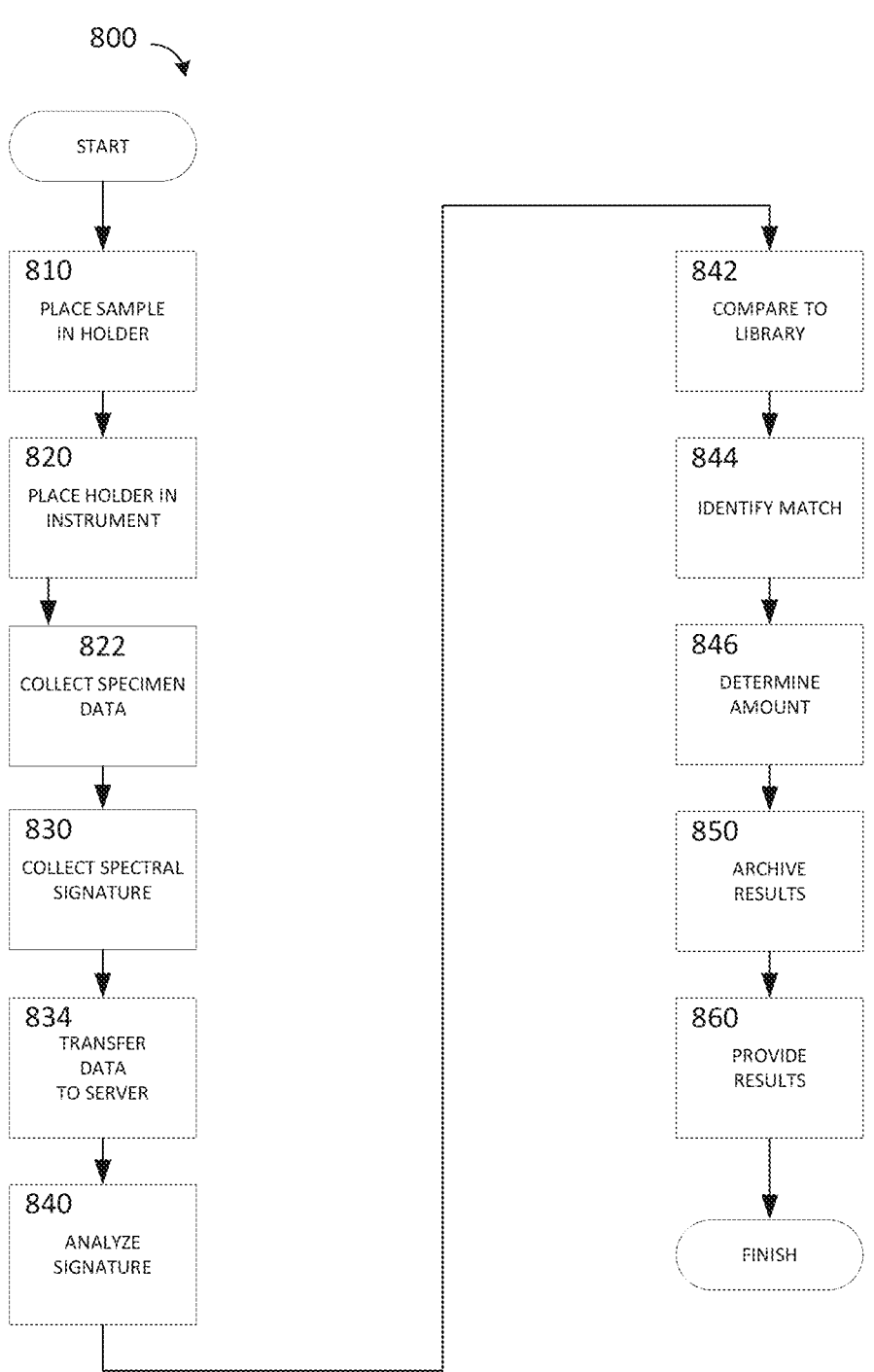
FIG. 8 depicts a flow chart of an exemplary method of use, according to certain aspects of the present disclosure.

FIG. 8 depicts a flow chart 800 of an exemplary method of use, according to certain aspects of the present disclosure. In the first step 810, a user places a sample of a material in the holder. This step may include closing a lid over the sample and, in certain embodiments, closing of the lid may be a one-time action, i.e., a non-reversable event. In step 820, the user places the holder in the instrument body. In step 822, the user performs set-up and data entry operations. In certain embodiments, one of steps 820 and 822 includes the instrument retrieving a unique identifier (ID) from the holder that was placed in the body and storing this ID. In certain embodiments, one of steps 820 and 822 includes determination of the current physical location of the instrument using a locating system, e.g., an internal global position system (GPB) module and storage of the location.

Once the instrument is fully configured for this sample, the user initiates the analysis of the sample in step 830. In certain embodiments, step 830 comprises one of more of collection of multiple spectral signatures using different frequencies of source light and collection of multiple spectral signatures using different optical filters to modify the light emitted by the sample. In certain embodiments, step 830 comprises stimulation of the sample, for example by exposure of the sample to one or more of a magnetic field, an electrostatic field, and a radio frequency (RF) field. In certain embodiments, step 830 comprises introduction of a fluid into the sample.

After the spectral signatures are collected, the instrument transfers a portion of the data, which includes one or more of the spectral signatures and information entered by the user and determined by the instrument, to a server that may be remote.

Software on the server analyzes the data in step 840, compares the results of the analysis to a library of signatures in step 842, and identifies a match between the sample and the materials of the library in step 844.

In step 846, the software on the server analyzes the spectral signatures and determines an amount of the matched material in the sample. In certain embodiments, the analysis determines an amount present only for a pre-determined material. In certain embodiments, the analysis may calculate a ratio of the amount of one material to the amount of another material.

Step 850 stores the results of the analysis and the data in a memory on the server. In certain embodiments, the memory is located separate from the server. In certain embodiments, the results are sent to the instrument and stored in a memory in the instrument or a removable drive, e.g., a thumb drive, attached to the instrument. The results are sent to the instrument in step 860 and provided to the user on the user interface. In certain embodiments, step 860 includes providing the information on one of a personal computer, a laptop, a tablet, a smart phone, or other display.

Figure 9A:
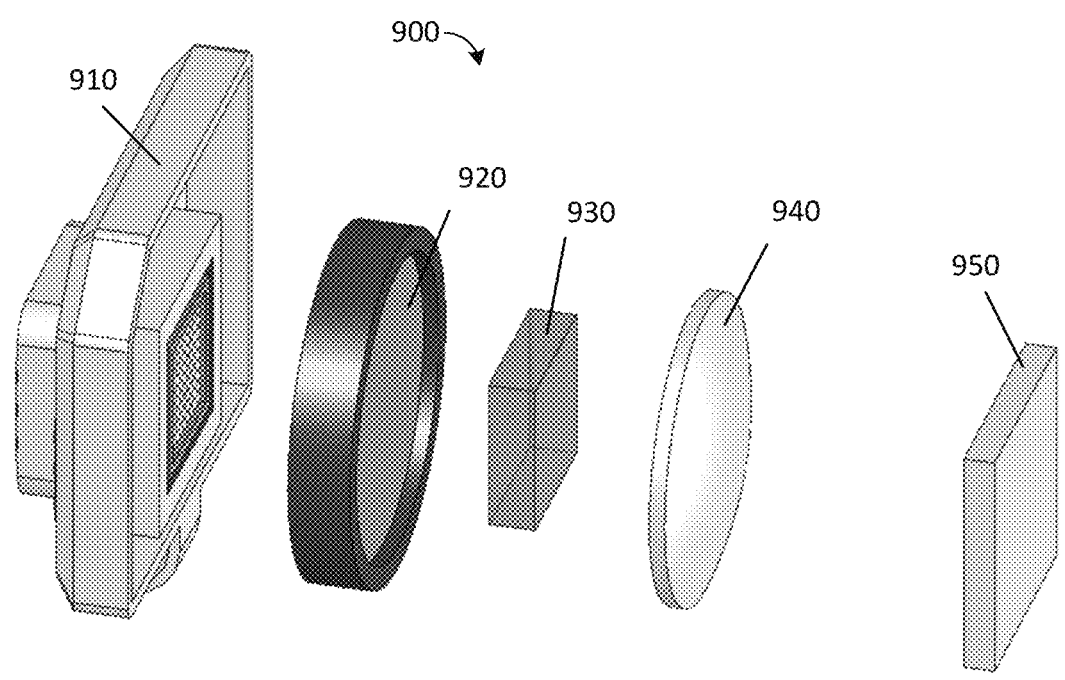
FIGS. 9A-9B depicts exemplary embodiments of an optical system of the apparatus, according to certain aspects of the present disclosure.

FIG. 9A depicts an exemplary embodiment of an optical system 900 of the apparatus, according to certain aspects of the present disclosure. In this embodiment, the system 900 comprises a holder 910, an optical filter 920, a grating 930, a focusing lens 940, and a detector 950. The optical filter 920 is configured to block the wavelength of the excitation light. The grating 930 separates the light emitted by the sample into its various wavelengths. The focusing lens 940 focuses each separated wavelength onto the detector 950 in a spatially separated position.

Figure 9B:
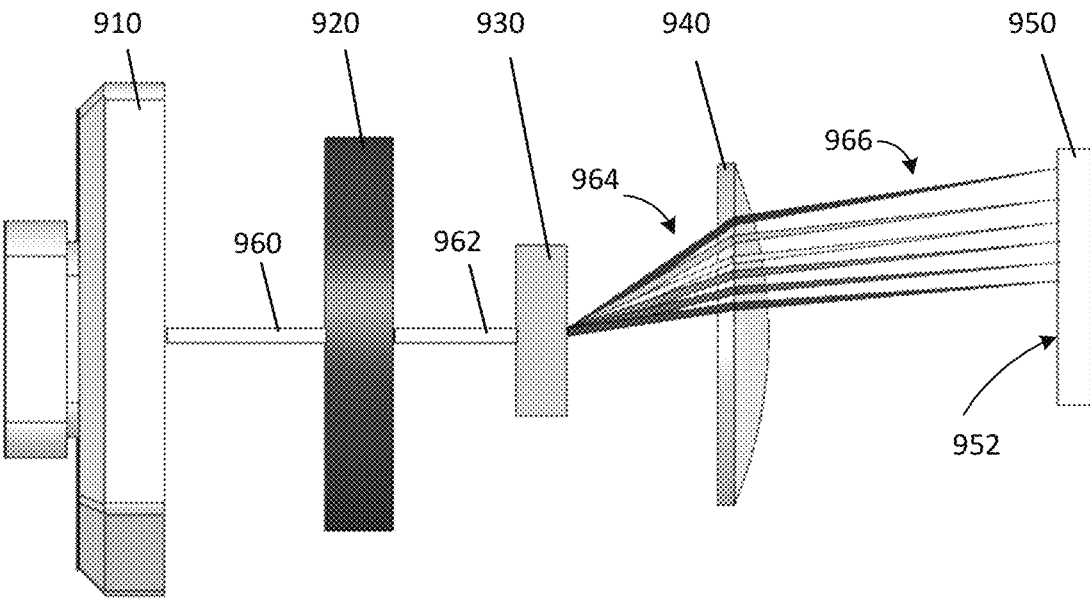

FIG. 9B depicts the passage of light emitted by the sample (not visible as it is located within the holder 910) through the optical system 900, according to certain aspects of the present disclosure. A single beam 960 of collimated light being emitted from the holder 910 is shown for clarity, although there are a plurality of adjacent beams of light coming from the holder 910 that are collimated and parallel to each other. After passing through the filter 920, the filtered light 962 strikes the grating 930 and a portion is transmissively refracted into a refracted beam 964. Each of the matching-wavelength spectral sub-component beams 964 of the plurality of adjacent beams of light that are exiting the grating 930 are still collimated and parallel to each other, i.e., all sub-components at the same wavelength will enter the focusing lens 940 at the same angle. For example, the green portions from the multiple beams are all collimated and parallel to each other as they enter the focusing lens 940. The focusing lens 940 focuses the spectral sub-component beams 964 into converging sub-component beams 966 that have foci on a plurality of spatially separate locations on the detector 950.

In certain embodiments, the focusing lens 940 comprises multiple elements for focusing and beam shaping. In certain embodiments, the focusing lens 940 comprises one or more of a curved mirror and a flat mirror. In certain embodiments, the detector 950 comprises one or more of a linear 1D array of sensing elements, e.g., pixels, and a 2D array of sensing elements.

Figures 10A, 10B, 10C:
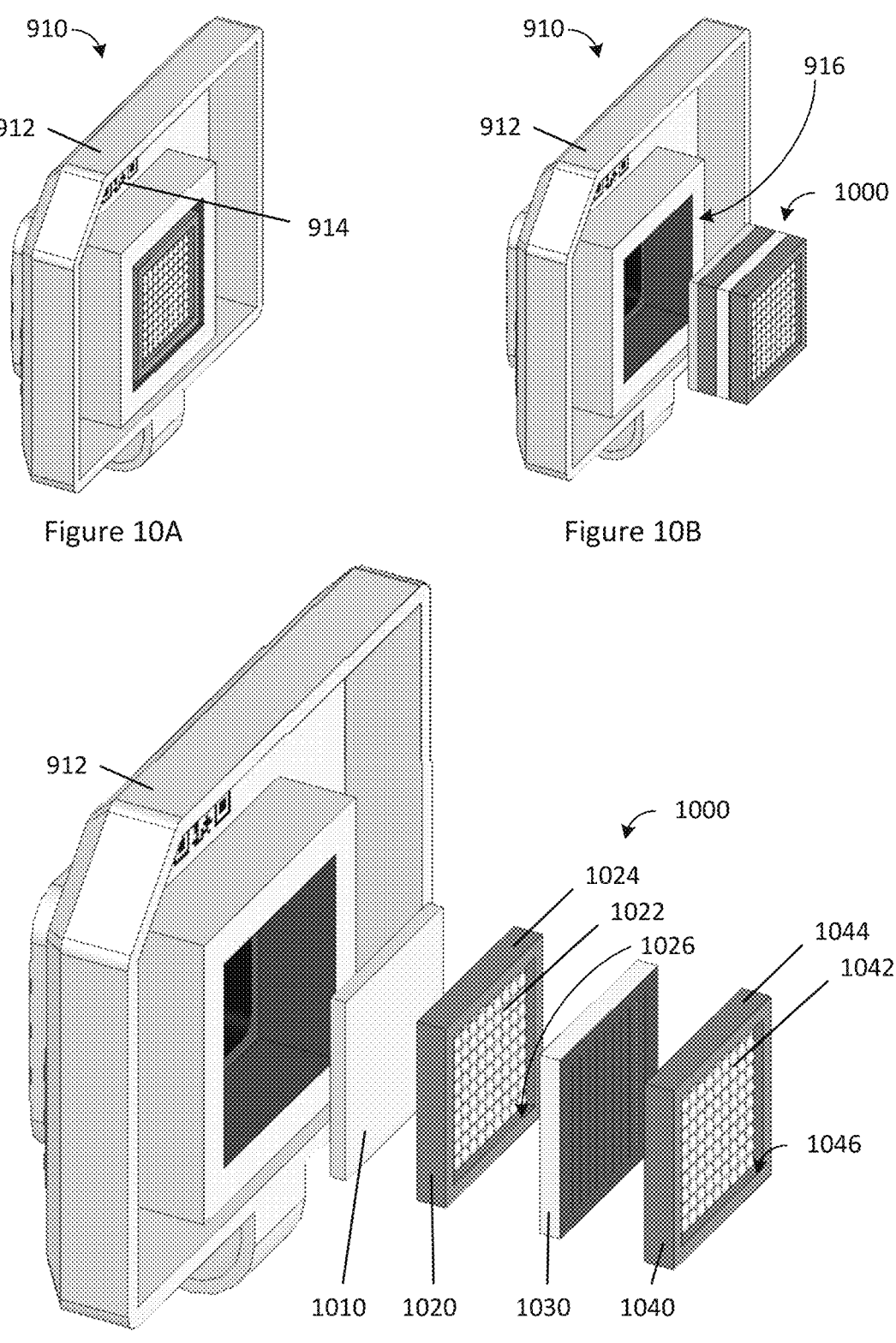
FIGS. 10A-10C depict an exemplary embodiment of a disposable holder, according to certain aspects of the present disclosure.

FIG. 10A depicts an exemplary embodiment of a single-use holder 910, according to certain aspects of the present disclosure. The holder 910 has a frame 912 on which is printed a unique identifier 914, e.g., a matrix code. In certain embodiments, the identifier 914 comprises a human-readable code. In certain embodiments, the identifier 914 comprises an electronic device, e.g., a ROM chip or an RFD chip, that stores the identifier.

FIG. 10B depicts an optical assembly 1000 removed from the cavity 916 of the holder. The cavity 916 is adjacent to a compartment (not visible in FIG. 10B) of the frame 912 that is configured to accept a sample of a material such that the sample is pressed against the optical assembly 1000.

FIG. 10C depicts an exploded view of an exemplary optical assembly 1000, according to certain aspects of the present disclosure. In this example, optical assembly 1000 comprises one or more of a sample plate 1010, a sample lens array 1020, a slit array 1030, and a collimating lens array 1040, each coupled to at least one of the adjacent component and to the frame 912. In this embodiment, the sample plate 1010 is an optically clear planar sheet that is disposed, when the optical assembly 1000 is mounted in the frame 912, proximate to the sample compartment such that the sample is in contact with a surface of the sample plate 1010. In certain embodiments, optical assembly 1000 comprises a sample plate 1010, a slit array 1030, and a collimating lens array 1040. Other embodiments of the sample plate are discussed with respect to FIGS. 12A and 12B.

The sample lens array 1020 comprises a plurality of focusing elements 1022 that are mounted in a frame 1024 with a set-back 1026 that provides clearance for the height of the focusing elements 1022 as well as a portion of a separation of the focusing elements 1022 from the next component. In certain embodiments, the focusing elements 1022 comprise one or more of spherical, aspherical, and diffractive optical components. In certain embodiments, the plurality of focusing elements 1022 are configured to collect light from a respective plurality of regions of the surface of the sample and produce a respective plurality of beams of light.

The slit array 1030 comprises one or more slits each having a width. In certain embodiments, a portion of the plurality of focusing elements 1022 is arranged in a straight row that is parallel to a slit of the slit array 1030 and the focusing elements of the row are configured to focus the respective beams of light on the slit. In certain embodiments, the plurality of focusing elements and the plurality of slits are arranged in a non-rectilinear pattern, e.g., concentric circles.

The collimating lens array 1040 comprises a plurality of collimating lenses 1042 mounted in a frame 1044 with a set-back 1046 that provides clearance for the height of the collimating lenses 1042 as well as a portion of a separation of the collimating lenses 1042 from the next component. In certain embodiments, a portion of the plurality of collimating lenses 1042 is arranged in a straight row that is parallel to a slit of the slit array 1030. Each collimating lens 1042 is configured to accept the refracted light emanating from one of the slits and modify the light to form a collimated beam of light. All of the modified plurality of beams of light are collimated in a common direction.

In certain embodiments, the diameter of the individual focusing elements 1022 and/or the collimating lenses 1042 is less than 125 μm. In certain embodiments, the focusing elements 1022 and/or the collimating lenses 1042 are holographic lenses. In certain embodiments, the use of holographic lenses in place of conventional lenses provides a 10× improvement in light capture. In certain embodiments, the use of holographic lenses in place of conventional lenses provides a 50× improvement in light capture. In certain embodiments, the use of holographic lenses in place of conventional lenses provides a 100× improvement in light capture.

In certain embodiments, the separation of the sample plate 1010 from the sample lens array 1020 is less than 5 mm. In certain embodiments, the separation of the sample plate 1010 from the sample lens array 1020 is less than 2 mm. In certain embodiments, the separation of the sample lens array 1020 and the slit array 1030 is less than 5 mm. In certain embodiments, the separation of the sample lens array 1020 and the slit array 1030 is less than 2 mm. In certain embodiments, the separation of the slit array 1030 and the collimating lens array is less than 5 mm. In certain embodiments, the separation of the slit array 1030 and the collimating lens array is less than 2 mm.

Figure 10D:
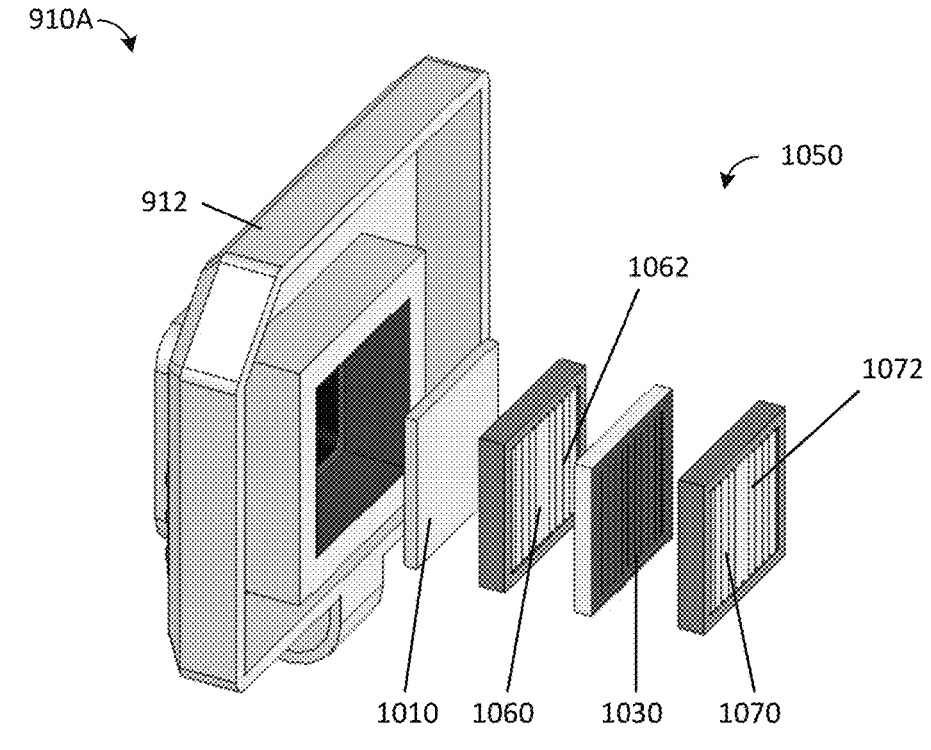
FIG. 10D depicts another embodiment of a disposable holder, according to certain aspects of the present disclosure.

FIG. 10D depicts another embodiment of a disposable holder, according to certain aspects of the present disclosure. The optical assembly 1000 of FIG. 10C is replaced by optical assembly 1050 that replaces sample lens array 1020 with a sample lens array 1060 and the collimating lens array 1040 with a collimating lens array 1070. Each column of individual lenses 1022 and 1042 is replaced by a cylindrical lens 1062 and 1072. Each cylindrical lens 1062 focuses light on one of the slits of slit array 1030 and the light emerging from each slit is collimated by one of the cylindrical lenses 1072.

With the cylindrical lens arrays of optical assembly 1050, the sample lens array 1060 captures light reflected from respective parallel areas of the sample and focuses the light onto a respective slit of slit array 1030. Compared to a conventional spectrometer, this arrangement captures light from a much larger area of the sample, in certain embodiments 2×, 5×, 10×, 20×, 50×, and 100× the amount of light, and consequently the intensity of the light from the sample is increased by approximately the same amount. An increase in intensity creates a stronger signal from the detector, thereby improving the measurement of small signals, e.g., values of Raman peaks.

The collimating lens array 1070 captures light that emerges from a respective slit of slit array 1030 and collimates the light in a direction common to all the cylindrical lenses 1072. With reference to FIG. 9B, the grating 930 will disperse the light from all collimating lenses 1072 at common angles, e.g., light of a common frequency is collimated in a single direction. The focusing lens 940 will focus light of a common frequency to a common location on the sensor 950. By gathering light from a large area of the sample, the intensity of the light at the sensor is proportional to a total area of the parallel areas of the sample from which reflected light is captured by the sample lens array 1060. This increase in intensity is effectively optical amplification increases the sensitivity of the analyzer in the same way that a larger diameter telescope is able detect dimmer stars by collecting more light from the sky. In certain embodiments, the intensity of the light at the sensor is 10× that of a conventional spectrometer having a single slit. In certain embodiments, the intensity of the light at the sensor is 20× that of a conventional spectrometer having a single slit. In certain embodiments, the intensity of the light at the sensor is 50× that of a conventional spectrometer having a single slit. In certain embodiments, the intensity of the light at the sensor is 100× that of a conventional spectrometer having a single slit.

In certain embodiments, the holder 910, or 910A, is separable from the main spectrometer, which contains one or more of the optical filter 920, the grating 930, the focusing lens 940, and the detector 950 as well as one or more of a light source, a power supply, a user interface, a processor, a memory, and other components (not shown in FIG. 9A) necessary to measure aspects of the light provided by the holder 910. In certain embodiments, one or more of the optical filter 920, the grating 930, the focusing lens 940 are provided as part of the holder 910 and therefore not part of the main spectrometer. In certain aspects, the body 912 comprises an interface configured to detachably mate with a spectrometer. In this manner, a plurality of holders 910, or 910A, may be used to capture a respective plurality of samples, wherein each holder 910 is sequentially mated to the spectrometer and the sample of that holder analyzed.

Figures 11A, 11B, 11C:
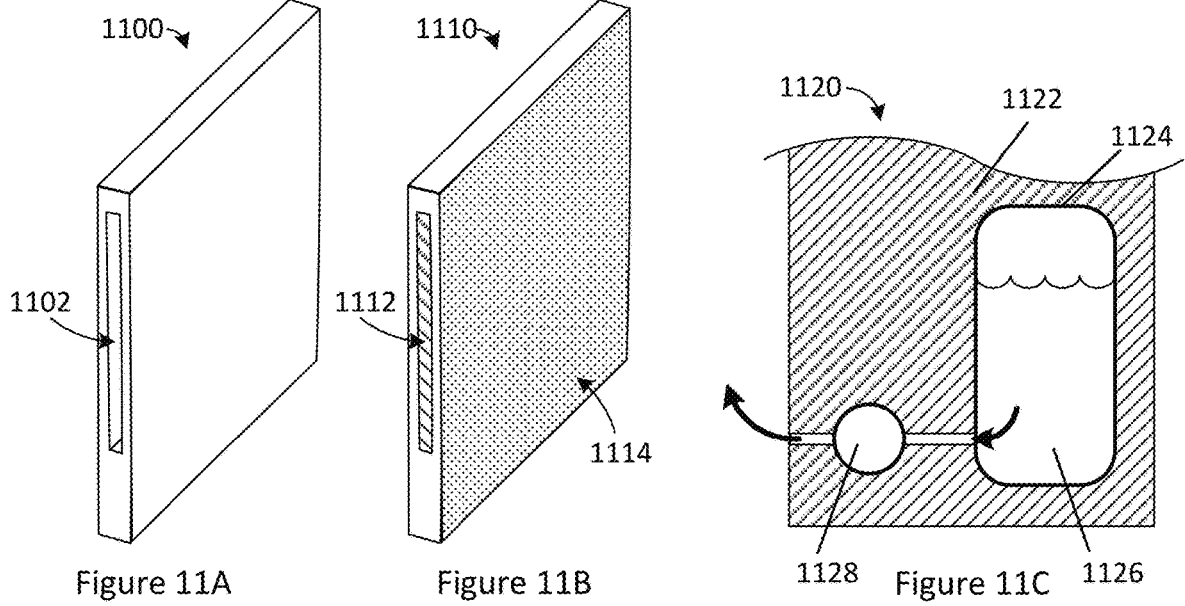
FIGS. 11A-11C depicts exemplary embodiments of a sample plate, according to certain aspects of the present disclosure.

FIG. 11A depicts an exemplary embodiment of a sample plate 1100, according to certain aspects of the present disclosure. The sample plate 1100 comprises a channel 1102 that is configured to accept a liquid sample (not shown in FIG. 11A). In certain embodiments, the channel 1102 passes through the width of the sample plate 1100 so as to form a passage through which a liquid sample can flow, thus enabling continuous monitoring of a stream to be periodically tested. In certain embodiments, the channel 1102 is a sealed compartment with entrance and exit ports (not shown in FIG. 11A) so as to facilitate introduction of a liquid sample into the channel 1102 and removal of air.

FIG. 11B depicts an exemplary embodiment of a sample plate 1110, according to certain aspects of the present disclosure. In certain embodiments, the sample plate 1110 comprises an actuator 1112 at least partially embedded in the sample plate 1110. In certain embodiments, the actuator 1112 is selected from the group of a temperature-control element, a filtering element, and a stimulation element. In certain embodiments, the temperature-control element can perform at least one of heating or cooling the sample. In certain embodiments, the filtering element can selectively allow or block selected frequencies of light. In certain embodiments, the stimulation element generates one of a magnetic field, an electrostatic field, and a dynamically oscillating electric field, e.g., a radiofrequency (RF) field. In certain embodiments, the sample plate 1110 comprises a coating 1114 on one or more surfaces. In certain embodiments, the coating 1114 functions as one or more of an optical filter, an electric shield, an antenna, and an electric conductor that may be patterned.

FIG. 11C depicts an exemplary embodiment of a sample plate 1120, according to certain aspects of the present disclosure. In certain embodiments, the sample plate 1120 comprises a reservoir 1124 embedded within the body 1122 of the sample plate 1120 and configured to contain a fluid 1126 and a pump 1128 fluidically coupled between the reservoir 1124 and a surface of the sample plate 1120 and configured to selectably expel a portion of the fluid 1126 from the sample plate.

Figure 12A:
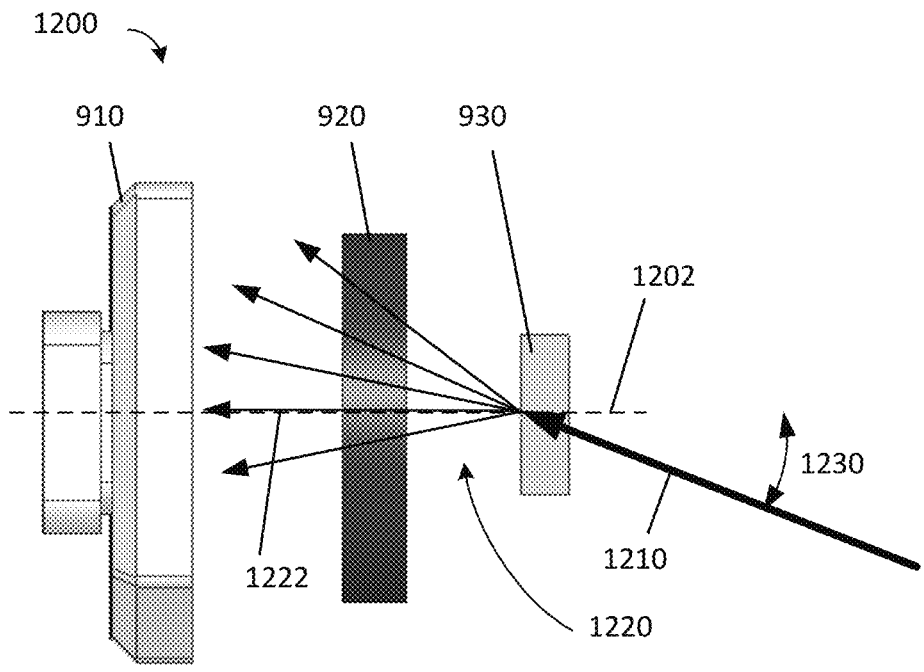
FIGS. 12A-12B depicts exemplary means of providing illumination of the sample, according to certain aspects of the present disclosure.
Figure 12B:
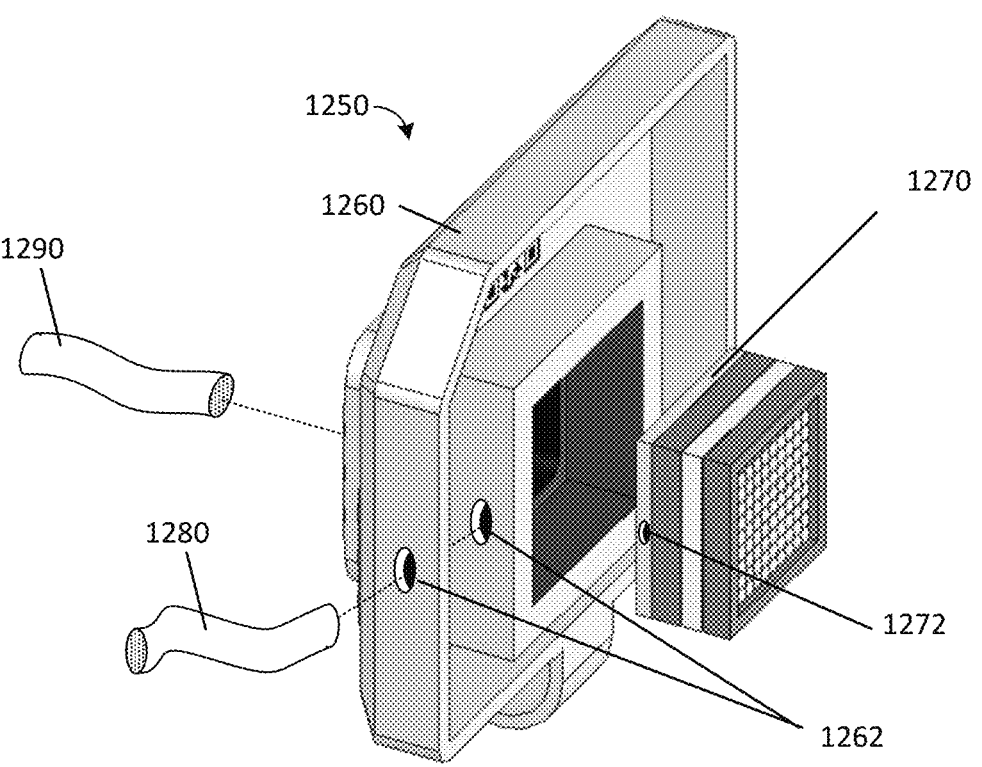

FIG. 12A-12B depicts exemplary means of providing illumination to the sample, according to certain aspects of the present disclosure.

FIG. 12A depicts a schematic of certain aspects of a novel Raman spectrometer 1200, according to certain aspects of the present disclosure. In this exemplary embodiment, an incident ray 1210 of coherent, monochromatic, unidirectional illuminating light strikes a transmissive diffraction grating 930 at an angle 1230. In certain embodiments, angle 1230 is selected such that one of the mode rays 1220 is directed along the optical axis 1202 of the spectrometer 1200. In certain embodiments, the angle 1230 is selected to direct a higher-order mode ray, for example a $1^{st}$-order ray 1222, along the optical axis 1202. In certain embodiments, the angle 1230 is selected to direct the primary ray along the optical axis 1202.

One advantage of the novel arrangement of the light source (not shown in FIG. 12A) is the elimination of the partially reflective mirror 630 shown in FIG. 6. As the light in a conventional spectrometer must be first reflected and then transmitted by the mirror 630, there is a loss of energy, normally about 50%, of the scattered light coming from the sample. Although the selected mode with have only a portion of the energy of the incident beam 1210, there is no energy loss in the optical path from the sample to the grating 930.

A second advantage of the spectrometer 1200 is the more compact arrangement of components, as the light source is now generally aligned with the long dimension of the device, while a conventional spectrometer 600 has a laser light source 632, which may be large and heavy, positioned on one side. Repositioning the source 632 in a conventional design requires additional optical elements, for example folding mirrors and rigid supporting structure, that add weight and cost.

Light passing through grating 920 from a first surface to a second surface on the opposite side of the grating 920 from the first surface is described as passing through the grating 920 in a first direction, regardless of the angle of the path of the light to a perpendicular reference axis, such as axis 1202. Similarly, light passing through grating 920 from the second surface to the first surface is described as passing through the grating 830 in a second direction regardless of whether the path of the light traveling in the second direction is parallel to the path of the light traveling in the first direction. The use of "first direction" and "second direction" are meant only to convey the general direction of transmission from one surface to another.

FIG. 12B depicts another exemplary embodiment of means of providing illumination of the sample, according the certain aspects of the present disclosure. In certain embodiments, a beam of illuminating light is provided via a fiber optic cable 1280, or functional equivalent, that passes through openings 1262 in the frame 1260 of holder 1250 and then into a receiving port 1272 of the sample plate 1270. This type of side illumination is known in optics and provides light output across the planar surface of the sample plate 1272.

In certain embodiments, the beam of illuminating light is provided via a fiber optic cable 1290, or functional equivalent, that passes through the holder 1250 from a backside and mates with a diffuser (not visible in FIG. 12B) within the frame 1260 and disperses the light across the planar surface of the sample plate 1270.

In certain embodiments, the illumination light is modulated, for example by driving the light source with a square wave, thereby producing periods of illumination of the sample, i.e., when the source is on, separated by intervals of dark, i.e., when the source is off. Sensing of the output of the detector is synchronized with the square wave, for example by recording the output only while the source is off and adding the recordings of multiple dark intervals. In certain embodiments, sensing of the output of the detector occurs during portions of both the illuminated periods and the dark periods and the respective sets of measurements are compared during analysis.

Certain embodiments of the disclosed Raman spectrometer incorporate a novel arrangement of a light source that introduces the light into the optical path of the apparatus by passing the light through the transmissive diffraction grating in direction opposite the direction of the light passing from the sample to the detector. This novel arrangement beneficially reduces the size and complexity of the optical path by eliminating components that are critical in conventional spectrometers.

Certain embodiments of the disclosed Raman spectrometer consolidate critical elements of the optical path into a single-use holder. Miniaturization of the optical elements and the use of arrays of lenses in place of single lenses enables precise alignment without requiring complex alignment techniques during manufacturing.

Material Analysis

Cannabidiol (CBD) is a phytocannabinoid discovered in 1940. It is one of 113 identified cannabinoids in cannabis plants, along with tetrahydrocannabinol (THC), and accounts for up to 40% of the plant's extract. CBD has been found to have beneficial medical effects, including relief from pain and stiffness. CBD may be supplied as an oil, a powder, or as a liquid suspension. The mechanism of action for its biological effects has not been determined. CBD does not have the psychoactivity of THC and is not listed as a proscribed substance.

Hemp is a subspecies of cannabis that contains significant levels of CBD and low levels of THC. The 2018 United States Farm Bill removed hemp and hemp extracts (including CBD) from the Controlled Substances Act. THC, on the other hand, is still listed under Schedule I under the Controlled Substances Act. Federal law classifies a plant as hemp and therefore exempt from the Controlled Substances Act if the THC content, specifically delta-9 tetrahydrocannabinol, is ≤0.3% by weight. This is echoed in the California Code of Regulations that require that hemp crops be tested for THC content prior to harvest and that a hemp crop found to contain more than this amount of THC must be destroyed.

Figures 13A, 13B, 14A, 14B, 14C:
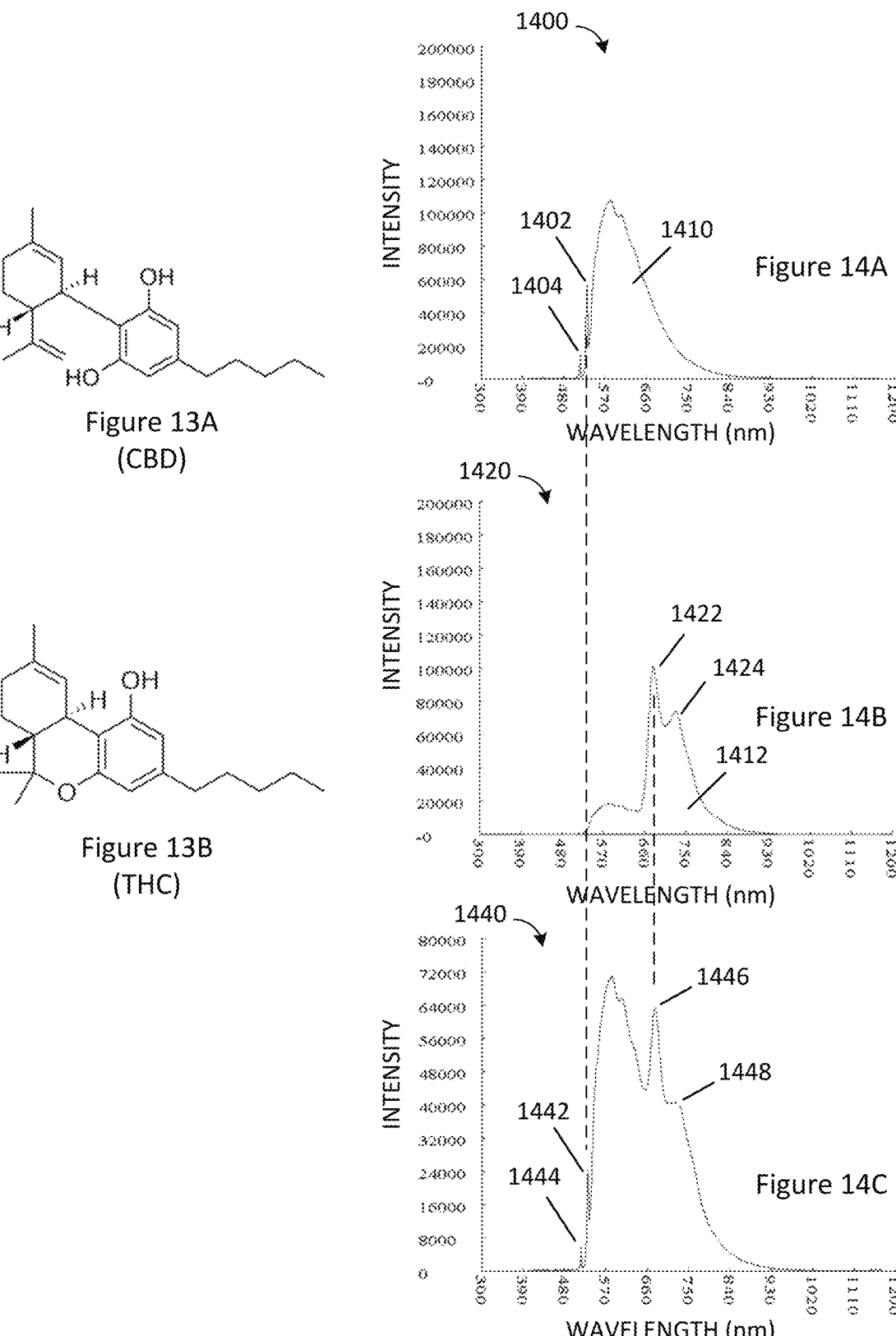
FIGS. 13A-13B are 2D representations of the chemical structures of CBD and THC.
FIGS. 14A-14C depict illustrative experimental results of the output of the analyzer, according to certain aspects of the present disclosure.

FIGS. 13A-13B are the 2D representations of the chemical structures of CBD and THC, respectively. It can be seen that while there is a great deal of structure in common, there are small differences in the composition and bond structure between CBD and THC that produce different Raman responses.

FIGS. 14A-14C present experimental results provided by the Raman analyzer disclosed herein.

Graph 1400 depicts the spectral response of a sample of CBD powder having ≤0.3% THC when illuminated with a source light having a wavelength of 515 nm. The x-axis is the frequency of the response in nanometers while the y-axis is an intensity. The response curve includes a large generally smooth portion 1410 that is the photoluminescence of the sample combined with narrow spikes 1402, 1404 that are Raman peaks associated with the chemical structure of CBD. In this experiment, peak 1402 has an intensity of approximately 60,000 and peak 1404 has an intensity of approximately 18000.

Graph 1420 depicts the spectral response of a sample of plant material containing approximately 47% by weight of THC when illuminated with a source beam of light having a wavelength of 515 nm. The curve includes the photoluminescence 1412, which has a markedly different shape that the photoluminescence 1410 of the CBD sample, and Raman spikes 1422 and 1424. In this experiment, peak 1422 has an intensity of approximately 100,000 and peak 1424 has an intensity of approximately 75000.

Graph 1440 depicts the spectral response of a sample consisting of a mixture of 40% of the powder of graph 1400 and 60% of the plant material of graph 1420 when illuminated with a source beam of light having a wavelength of 515 nm. Peaks 1442, 1444 correspond to peaks 1402, 1404 and peak 1446 corresponds to peak 1422. Peak 1442 has an intensity of approximately 24000, peak 1444 has an intensity of approximately 7000, and peak 1446 has an intensity of approximately 64000. The shoulder 1448 corresponds to the peak 1424 but does not provide a distinct peak.

In certain embodiments, the ratios of the intensities of corresponding peaks provides a measure of the amount of the associated material in the sample. In this case, the values of corresponding peaks and their respective ratios are shown in Table 1.

TABLE 1

| PEAK-A | INTENSITY | PEAK-B | INTENSITY | RATIO |
|--------|-----------|--------|-----------|-------|
| 1442 | 24000 | 1402 | 60000 | 0.4 |
| 1446 | 64000 | 1422 | 105000 | 0.6 |

The ratio of peaks 1442/1402 represents the relative amount of the CBD powder in the mixture of graph 1440 and the ratio of peaks 1446/1422 represents the relative amount of the THC-containing plant material powder in the mixture. The respective ratios of 0.4, 0.6 are complementary and together support an assessment that the mixture is approximately 40% CBD powder and 60% plant material.

This data demonstrates the principle of establishing "fingerprints" of two reference materials and then being able to determine the proportions of a mixture of the two materials using this analyzer disclosed herein. In certain embodiments, the determination compares the magnitudes of one or more Raman peaks of a measurement of a sample of the mixture to the fingerprints. In certain embodiments, the determination compares attributes of the overall response curve to the fingerprints. In certain embodiments, the attribute is a curve value at a specific wavelength or wave number. In certain embodiments, the fingerprint is a computational prediction of a wavelength or wave number of a Raman peak based on one or more aspects of the chemical structure of a reference material.

It must be noted that the measurement made by the disclosed apparatus is based on the surface area of the sample illuminated by the light source and examined by the sensor of the disclosed apparatus while the limit of THC content is provided as a weight percentage. Conversion of the sensed results to a weight percentage is accomplished by use of reference samples that have been characterized by an accepted standard process, for example liquid chromatography coupled with mass spectrometry. In the example of FIGS. 14A-14C, the THC content of the plant material was determined by a third party using an accepted laboratory process and the THC content of the mixture of graph 1440 is therefore 60% of 47%=0.28% by weight.

The wavelengths of the various attributes of the spectral response of a sample are related to the wavelength of the source light. In addition, the shape and overall intensity of the photoluminescence may be different depending on the wavelength of the source beam. The graphs of FIG. 14A-14C, for example, are produced by a source beam of 515 nm. In certain embodiments, the frequency of the source beam is selected to maximize the visibility of a Raman peak, i.e., to provide the greatest difference between the intensity of a Raman peak and the intensity of the photoluminescence at and around the frequency of that Raman peak. In certain embodiments, the frequency of the source beam is selected to maximize the visibility of a particular Raman peak that is characteristic of a target molecule.

In certain embodiments, measurements are made with a plurality of light sources having a respective plurality of wavelengths. In certain embodiments, the plurality of wavelengths are selected to each maximize the visibility of one of a plurality of Raman peaks characteristic of a target molecule. In certain embodiments, the intensity of a Raman peak is determined only when the source light is the wavelengths selected to maximize the visibility of that Raman peak. In certain embodiments, the intensity of a Raman peak of a reference sample is determined at the same wavelengths as selected to maximize the sample. In certain embodiments, the ratios of a plurality of Raman peaks to their corresponding peak of a reference standard made with the same wavelengths of source light are combined to produce a composite value of the amount of a target material present in a sample.

In certain embodiments, the intent of the analysis of the spectral response is not to identify a material within a sample and is simply to determine the amount of a pre-determined molecule is present. For example, a sample of a hemp plant is analyzed to determine the amount of THC present in the sample. In another example, a sample of a food product is analyzed to determine the amount of a pre-determined pesticide in the sample. In another example, a sample of a wine is analyzed to determine the amounts of pre-determined molecules in the sample, wherein the pre-determined molecules are associated with the one or more of the taste, smell, and texture of wine.

Sample Holder

Figure 15A:
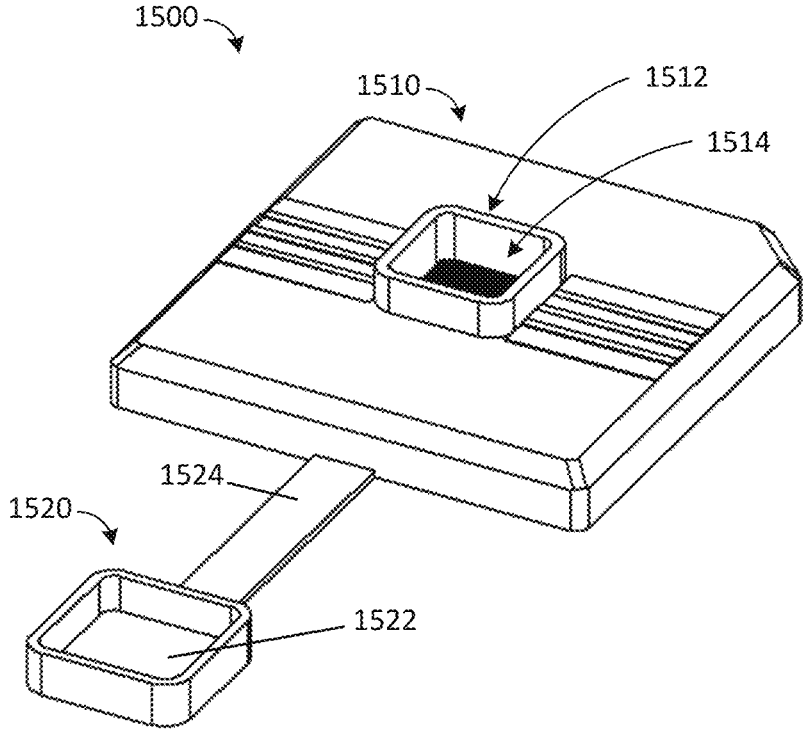
FIGS. 15A-15B depict an exemplary sample container, according to certain aspects of the present disclosure.

FIG. 15A depicts an exemplary sample holder 1500 in an open configuration, according to certain aspects of the present disclosure. The holder 1500 has a body 1510 with an access opening 1512 into a sample compartment 1514. The cap 1520 has an interior surface 1522 and is connected to the body 1510 by a strap 1524. In certain embodiments, the cap 1520 is separate from the body 1510.

Figure 15B:
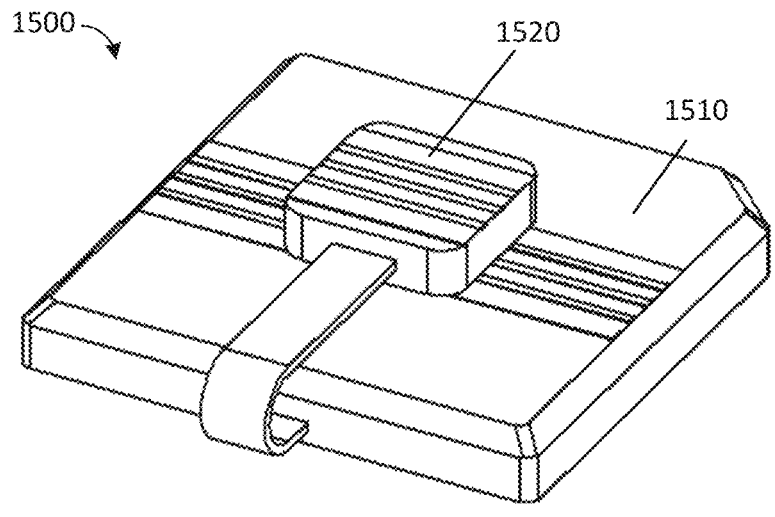

FIG. 15B depicts sample holder 1500 in a closed configuration, wherein the surface 1522 of cap 1520 seals the opening 1512. In certain embodiments, the materials of one or more of the body 1510, the contact surface of opening 1512, cap 1520, and surface 1522 are selected to maintain a controlled environment in the compartment 1514. In certain embodiments, one or more of the body 1510, the contact surface of opening 1512, cap 1520, and surface 1522 comprise a coating. In certain embodiments, the contact surface of opening 1512 and surface 1522 comprise a sealing material, for example a gasket, to enhance the sealing of the opening 1512.

Tamper-Evident Sample Holder

Figures 16A, 16B, 16C:
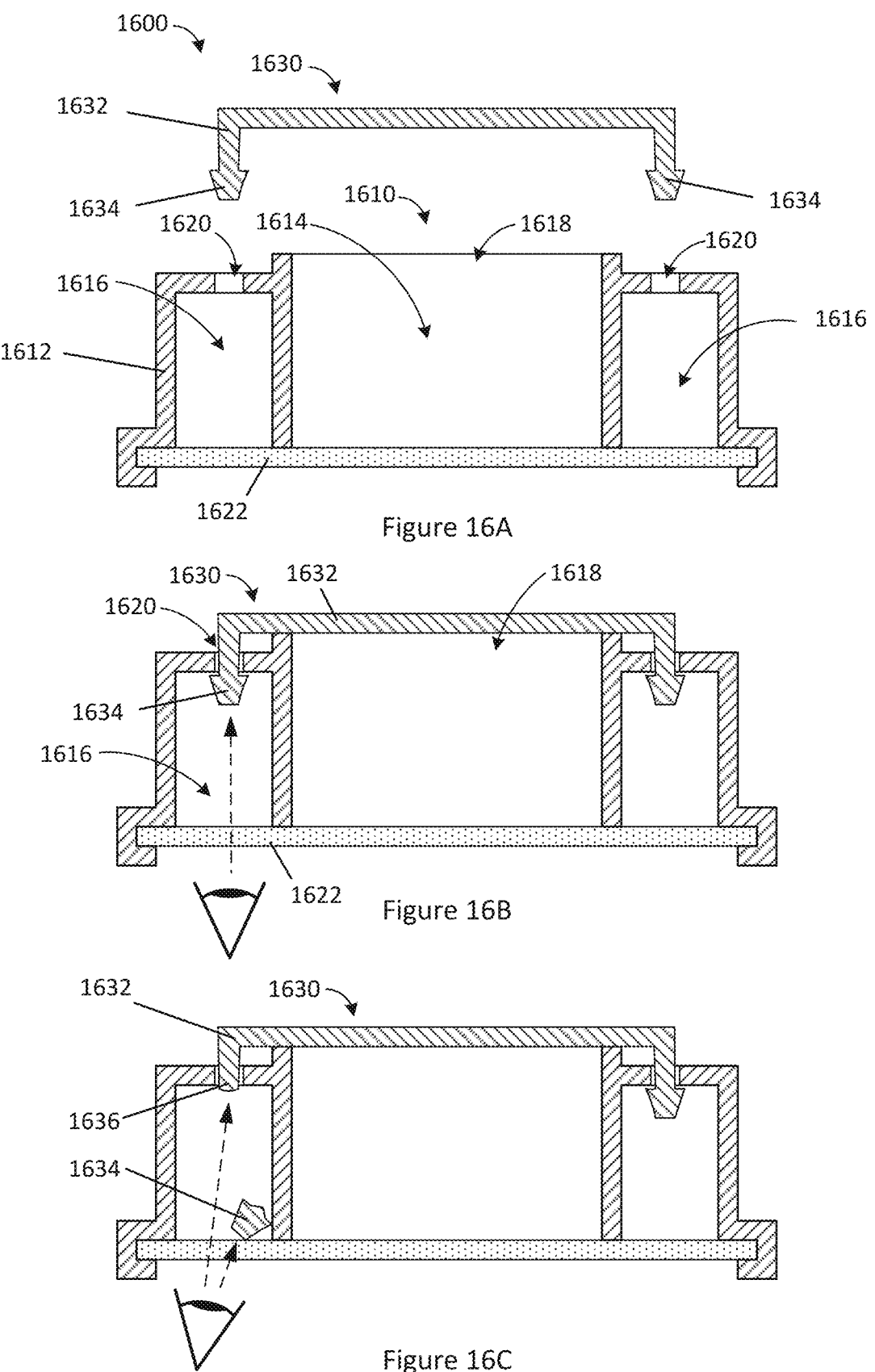
FIGS. 16A-16C depict an exemplary tamper-evident sample container, according to certain aspects of the present disclosure.

FIG. 16A depicts an exemplary tamper-evident sample holder 1600, according to certain aspects of the present disclosure. In certain embodiments, the holder 1600 comprises a body 1610 having a sample compartment 1614, a closure compartment 1616, and a window 1622 providing visibility into one or more of the sample compartment 1614 and the closure compartment 1616. There is an access opening 1618 to the sample compartment 1614 and a latch opening 1620 to the closure compartment 1616. There is a cap 1630 with a body 1632 coupled to a non-return fitment 1634. In certain embodiments, the sample compartment 1614 is separated from the closure compartment 1616 such that a sample placed in the sample compartment 1614 does not obscure the visibility of the latch opening 1620 through the window 1622. In certain embodiments, there is no access into the closure compartment 1616 regardless of whether the cap 1630 is installed on the body 1612. In certain embodiments, window 1622 is replaced by separate windows (not shown) respectively covering the sample compartment 1614 and closure compartment 1616. In certain embodiments, the window 1622 is implemented as an opening (not shown) from the exterior into the latching compartment 1616 that provides visibility of the inside of latching opening 1620 while preventing access to the interior of the latching compartment as well as preventing a broken-off fitment 1634 (see FIG. 16C) from coming out of the latching compartment 1616. In certain embodiments, a portion of window 1622 comprises a transparent material and is sealed to the body 1612 such that a sample in compartment 1614 is protected from contamination.

The disclosed holder 1600 comprises a tamper-evident feature that provides residual physical evidence when the sample compartment 1614 has been accessed. In the absence of this evidence, it can be presumed that the sample has not been tampered with since originally placed within the compartment and the cap 1620 sealed to the body 1632.

FIG. 16B depicts the holder 1600 with the cap 1632 disposed in the closure position relative to the body 1610, wherein the body 1632 is configured to seal the access opening 1618. The fitment 1634 has passed through the latching opening 1620 to a latched position within the closure compartment. The fitment 1634 is visible through the window 1622 while in the latched position such that a user can verify that the fitment 1634 is intact and in the intact location so as to verify that the cap 1630 has not been removed, indicating that a sample contained in the sample compartment 1614 is undisturbed.

FIG. 16C depicts the holder 1600 after the cap 1630 has been removed and replaced. The cap 1630 is configured such that fitment 1634 separates from the body 1632 when the cap 1630 is dislodged from its closure position. The fitment 1634 is retained in the closure compartment 1616 when separated from body 1632 such that a user can see the broken-off fitment 1634 and verify that the fitment is not in the intact position of FIG. 16B. Further, the fitment 1634 is not accessible without further damage to the window 1622 or body 1612, thus preventing returning the broken-off fitment 1634 to the intact position, for example by gluing it to the stub 1636 of cap 1630.

If a user attempts to remove the cap 1630 and replace it with a new undamaged cap (not shown), the new cap will present a fitment in the latched position but the broken off fitment 1634 of FIG. 16C will still be present, thus indicating that the sample has possibly been tampered with.

Determination of Sample Location

Figures 17A, 17B, 17C:
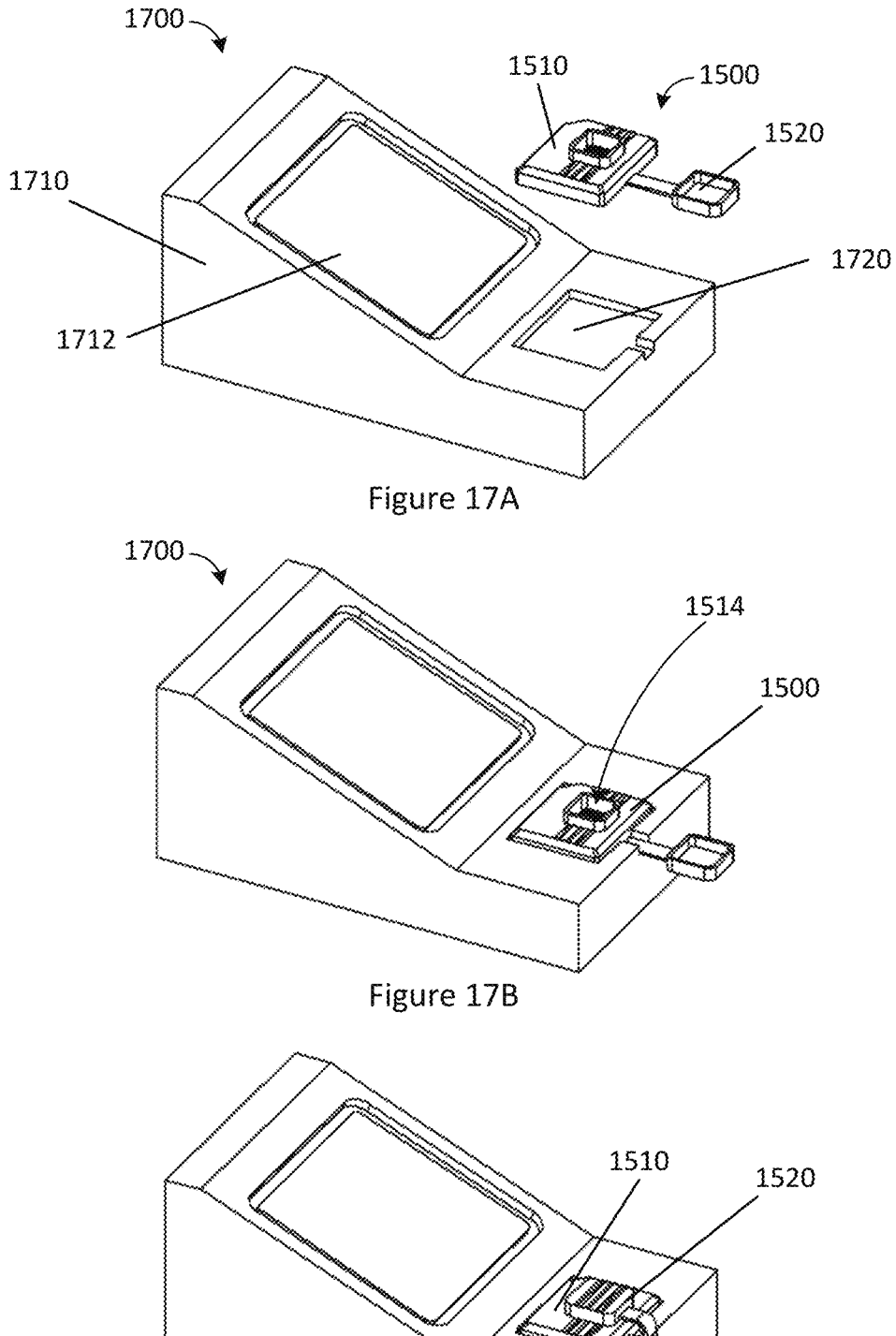
FIGS. 17A-17C depict an exemplary sample capture device, according to certain aspects of the present disclosure.

FIGS. 17A-17C depict an exemplary sample capture device 1700, according to certain aspects of the present disclosure.

FIG. 17A depicts the sample capture device 1700 as having a body 1710 with a user interface 1712. In certain embodiments, the user interface 1712 is a graphic user interface with a touchscreen overlay. In certain embodiments, the user interface 1712 comprises a keypad having one or more of numeric and alpha keys, wherein the keypad can be virtual or hardware. The body 1710 further comprises a recess 1720 configured to accept a material sample holder, for example the sample holder 1500 shown in FIGS. 15A-15B wherein the body 1510 fits into the recess 1720. In certain embodiments, the device 1700 is coupled to a secondary device, for example a mobile phone or a laptop (not shown) and the secondary device provides the user interface.

FIG. 17B depicts the sample capture device 1700 with a sample holder 1500 disposed in the recess 1720. A user is now able to place a sample of a material in the compartment 1514. The user then closes the cap 1520 and secures it to the body 1510, thus sealing the sample in the compartment 1514.

Figure 18:
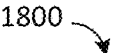
FIG. 18 depict an exemplary block diagram of the sample capture device, according to certain aspects of the present disclosure.

FIG. 18 depict an exemplary block diagram 1800 of the sample capture device 1700, according to certain aspects of the present disclosure. In certain embodiments, the device 1700 comprises a scanner 1734 that scans an identifier 1540 on the sample holder 1500 and a sensor 1732 that detects whether the cap 1520 has been secured to the body 1510 of sample holder 1500. In certain embodiments, the device 1700 also includes a camera 1736 and a GPS module 1738 and a communication module 1742 configured to communicate with external devices, for example a server 1750, over conventional wired and/or wireless networks and communication systems. The device 1700 comprises a memory 1740 is disposed within the body 1710. In certain embodiments, the memory is remote. In certain embodiments, memory 1740 contains instructions that, when loaded into the processor 1730 and executed, will cause the processor 1730 to perform one or more of the following actions:

receive information associated with latch 1530 from the sensor 1732 receive information associated with identifier 1540 from scanner 1734 receive the current location of the device 1700 from the GPS module 1738 receive information associated with the user and/or sample from the user interface 1712 receive an image from the camera 1736 store a portion of the received information in a memory, for example memory 1740 provide a portion of the received information to an external system, for example server 1750, over a known communication system such as Wi-Fi or a cellular network An exemplary use of the sample capture device 1700 is to take the device 1700 into a field planted with a plant and collect one or more samples of the plants for later evaluation. The user enters information associated with this field through the user interface 1712, for example the user, the field identification, a company farming the field, and the plant. In certain embodiments, the device 1700 captures the identification of the user through an alternate method, for example facial recognition through a camera, scanning a barcode, or detection of an RFD-enabled badge. The user places an empty sample holder 1500 in the sample capture device 1700. The user takes a picture with the camera 1736 of a plant from which a sample will be collected. The user collects a portion of a plant and places the portion in the compartment 1514 of the sample holder 1500, then closes the cap 1520 and secures it in place. The device 1700 detects the closure of the cap 1520, which triggers the processor 1730 to receive the identifier 1540 from the scanner 1734 and the physical location from the GPS module 1738. The processor 1730 stores the entered and received information in the memory 1740 along with the date and time to create a data record associated with this sample. In certain embodiments, a portion of the data record is copied to the server 1750. The user then removes the sample holder 1500 from the sample capture device 1700 and places the sample holder 1500 in a transfer container. The user need not mark the sample holder or provide special handling to maintain a record of where the sample was collected or protect the sample. In certain embodiments, the sealed sample holder 1700 provides a traceable and tamper-evident container that can be transferred to an analysis device or a testing service. In certain embodiments, the sample holder is configured to provide a stable environment in order to reduce changes in the sample over time. In certain embodiments, the sample holder 1500 is archived as a long-term record of the sample and measurement.

In certain embodiments, the instructions in memory 1740, or software running on the server 1750 or another device such as a tablet or personal computer, uses the data record to provide a map showing the location of the sample collection.

Absorbance Spectrometry

In absorbance spectrometry, a material sample is illuminated with a beam of incident light. The material absorbs the light and re-emits a portion of the absorbed energy as light of a frequency determined by the molecular structure of the material. The spectral response of the emitted light will have peaks a resonant frequencies associated with specific types of bonds and structures. These peaks can be measured and compared to reference spectral responses of known reference materials to determine the contact of a reference material in a sample, much as discussed with respect to FIG. 14A-14C.

Figure 19A:
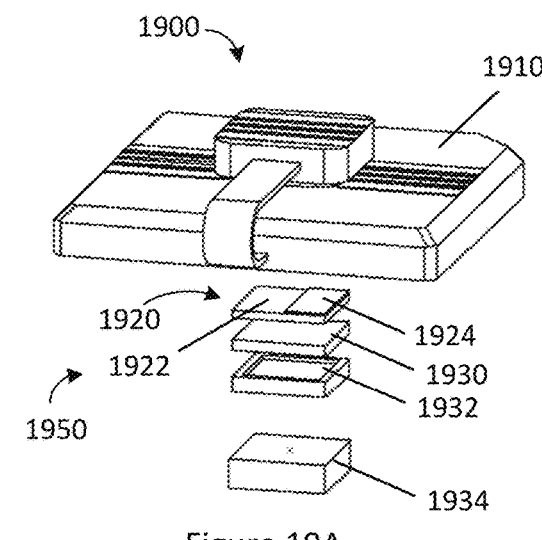
FIGS. 19A-19B depict an exemplary sample holder configured for analysis based on absorbance of light, according to certain aspects of the present disclosure.

FIG. 19A depicts an exploded view of an exemplary sample holder 1900 configured for analysis of a sample based on absorbance of light, according to certain aspects of the present disclosure. The holder 1900 has a body 1910 that is similar to the body 912 of FIG. 10D. The optical assembly 1050 of FIG. 10D is replaced by an optical assembly 1950 comprising a cover slip 1920, a slit array 1930, an array of collimating lenses 1932, and optionally a grating 1934. In certain embodiments, the cover slip 1920 has a transparent body 1922 with a reflective layer 1924 covering a portion of the body 1922.

Figure 19B:
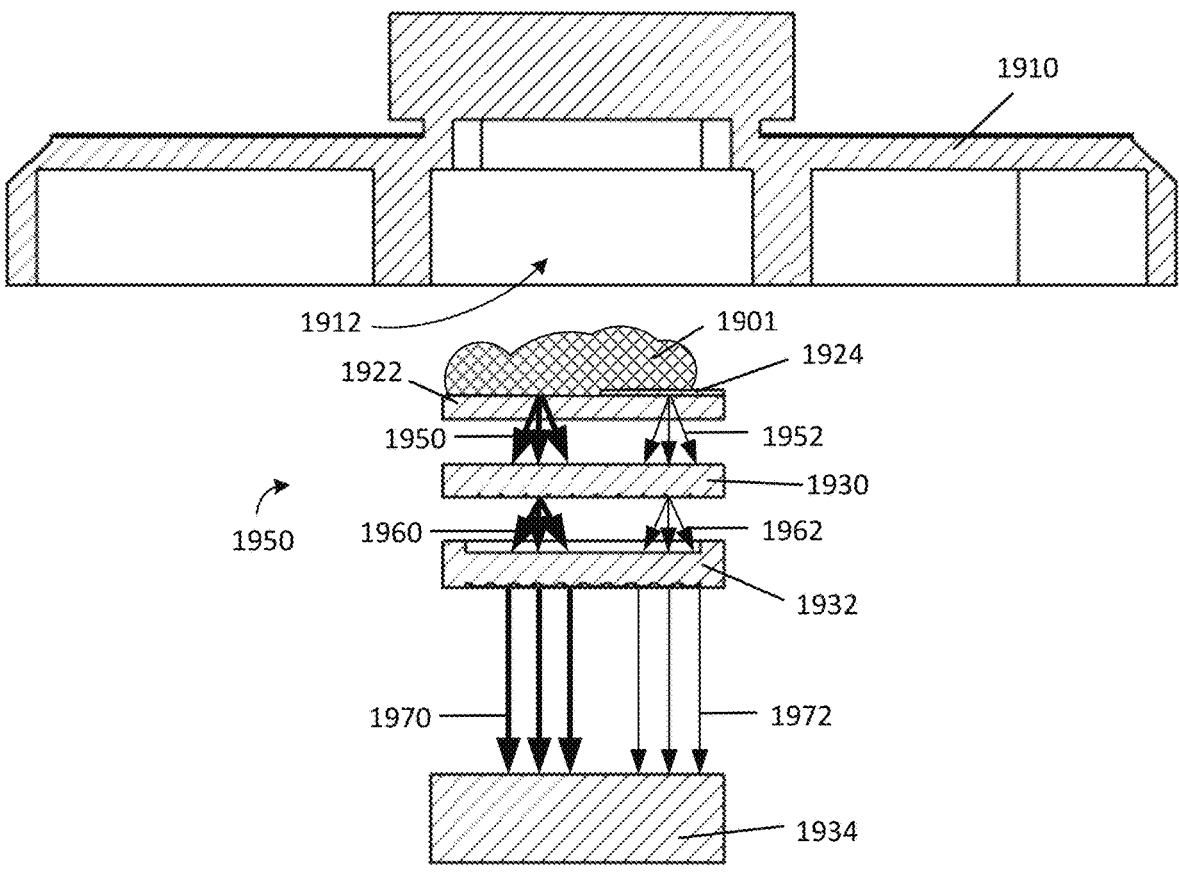

FIG. 19B depicts an exemplary illustration of how light emitted by the sample 1901 passes through the elements of optical assembly 1950. A sample of material 1901 is placed into compartment 1912 that is covered by the optical assembly 1950. In the exploded view of FIG. 19B, the sample 1901 is shown as located such that the underside of the sample 1901 is in contact with the upper surface of the cover slip 1922, as it would be in actual use. Although the incident light is omitted from FIG. 19 for clarity, a beam of excitation light is directed upward (in the orientation of FIG. 19A) to illuminate the underside of cover slip 1920 over both reflective layer 1924 and the remaining unobstructed portion of cover slip 1920. In certain embodiments, the excitation light has a specific wavelength, for example having passed through a selectable filter or generated by a light source that emits light having a narrow bandwidth of light about that wavelength. An example source light is light from a laser that emits light with a nominal wavelength of 532 nm that is passed through a 527-537 nm bandpass filter to produce a narrow-band beam of excitation light that is directed to the sample. In certain embodiments, the sample is serially observed using a plurality of wavelengths of excitation light, for example using a filter wheel comprising a plurality of optical filters.

The light 1950 that is emitted by the sample 1901 is radiated (shown as thick arrows) through the coverslip over a solid angle. A portion of the incident light is reflected by the reflective layer 1924 to produce reference light 1952 (thin arrows). The light 1950 and 1952 both pass through the slit array 1930, whereupon each slit illuminated by light 1950 emits light 1960 and each slit illuminated by light 1952 emits light 1962, which are then respectively focused by the array of collimating lenses 1932 into collimated beams of light 1970 from the sample 1901 and light 1972 from the reflective surface 1924. The collimated beams 1970, 1972 are optionally passed through a grating 1934 to spatially separate the light by wavelength as discussed with respect to FIG. 6.

The light beams 1970 and 1972 are spatially separated such that beam 1970 can be measured separately from beam 1972, whereupon the measured characteristics of the reference beam 1972 can be used to calibrate the sensor used for light 1970 or to interpret the measurement of light 1970. In certain embodiments, the beams 1970, 1972 may be alternately directed to a common sensor (not shown in FIG. 19B). In certain embodiments, a sliding mask (not shown in FIG. 19) or functional equivalent is provided at a point along the optical path from the cover slip 1920 to the grating 1934 to enable a user to direct the collimated light from either the sample or the reflective surface to the detector such that the detector observes only the reflective surface rays, which provides a reference signal suitable for calibration of the system, or only the sample emission rays.

Analysis System

The disclosed system provides secure handling and storage of the spectral results provided by the analyzer as well as further analysis and secure handling and storage of the analysis results.

Figure 20:
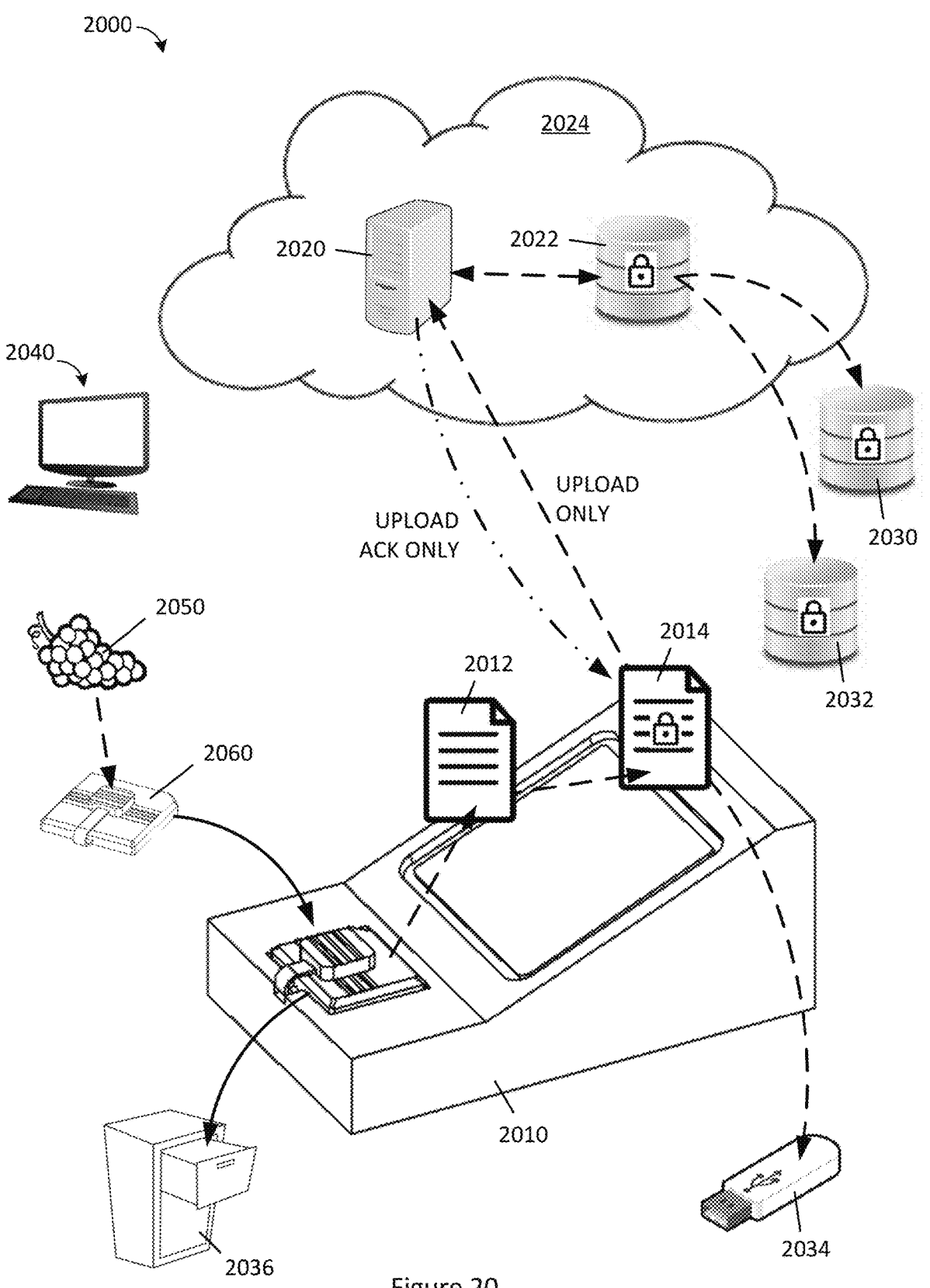
FIG. 20 is a schematic representation of an exemplary analysis system, according to certain aspects of the present disclosure.

FIG. 20 is a schematic representation of an exemplary analysis system 2000, according to certain aspects of the present disclosure. In an exemplary use model, a user places a sample of the material 2050 to be analyzed into a holder 2060. The holder 2060 carries a coded marker, e.g., a 2D matrix code, that comprises a holder identifier that is uniquely associated with the holder 2060. In certain embodiments, the marker also comprises one or more of a record of a pre-paid service, a date, a time, a lot number, a model number, and a location code. A sample 2050 of a material, e.g., a plant material, is loaded into the holder 2060, which is then loaded into the analyzer 2010.

The analyzer 2010 produces a data record 2012 each time that a sample 2050 is analyzed. In certain embodiments, the analyzer 2010 comprises a camera (not shown) that can be used to capture a picture of the sample 2050 prior to being loaded into the holder 2060. The data record 2012 comprises the measurements made by the analyzer 2010, the picture of the sample 2050, and a record identifier uniquely associated with the record 2012. Repetitive analysis of a common sample 2050 will create multiple records 2012 having unique record identifiers. In certain embodiments, the record identifier comprises a portion of the holder identifier. In certain embodiments, the record identifier comprises information associated with the analysis, e.g., a date, a time, a location, a user identifier, and manually entered information. In certain embodiments, the analyzer comprises a GPS subsystem and the location comprises the GPS location of the analyzer 2010 at the time of the analysis. In certain embodiments, the data record 2012 is stored only in volatile memory, e.g., a random access memory (RAM) of the processor in the analyzer 2010. In certain embodiments, the analyzer 2010 is configured such that the data record 2012 is not accessible.

After a sample 2050 is analyzed, the holder 2060 is removed from the analyzer 2010. In certain embodiments, the holder 2060 is moved to a sample archive 2036.

The data record 2012 is encoded using any known scheme, e.g., public key cryptography or a symmetric algorithm such as the Advanced Encryption Standard (AES) using a key of 128 bit or more, that produces an encrypted file 2014 resistant to viewing of the original data record 2012 without a predetermined "key." In certain embodiments, the data record 2012 uses a proprietary format and the name of the encrypted file 2104 includes an extension, e.g., ".ERA," that is not associated with existing software. In certain embodiments, the encrypted file 2014 comprises a first authentication parameter, e.g., a cyclic redundancy check (CRC) value, that enables verification of the integrity of the data record 2012 when decrypted. In certain embodiments, the encrypted file 2014 comprises a transmission verification parameter than can be used to verify the integrity of the transmitted file 2014 without decrypting the file 2014.

The combination of the tamper-evident feature and the holder identifier of the holder 2060, the data record identifier of the data record 2012 that comprises a portion of the holder identifier, and the authentication parameter of the encrypted data file 2014 provide chain-of-custody evidence that the data record 2012 are associated with the sample 2050 even after transfer and storage across multiple devices. Establishing a verifiable linkage from the sample to the results is essential to legal compliance, if the material is subject to regulation, and/or confidence by the end-user. Tampering with the sample 2050 and alteration of the holder identifier can be determined by visual inspection. The association of the data record 2012 with the specific holder 2060 is established by inclusion of at least a portion of the holder identifier in the data record 2012. The integrity of the data record 2012, including the identity of the holder 2060, can be verified using the authentication parameter. Encryption of the data record 2012 and inclusion of an authentication parameter within the encrypted file ensures that the record is not altered by a $3^{rd}$-party.

In certain embodiments, the encrypted file 2014 is stored on non-volatile memory, e.g., a solid state drive (SSD) in the analyzer 2010. In certain embodiments, the analyzer 2010 does not have the key required to de-crypt the encrypted file 2014, thereby ensuring the security of the data record 2012. In certain embodiments, the original un-encrypted data record 2012 is erased immediately after the encrypted file 2014 is created. In certain embodiments, the erasure comprises overwriting the memory space in the RAM where the data record 2012 was stored. In certain embodiments, the encrypted file 2014 can be copied to a secondary non-volatile memory, e.g., a USB memory stick 2034, thus enabling transfer and backup of the encrypted file 2014 without providing access to the data record 2012.

The encrypted file 2014 is transferred to a server 2020, e.g. a virtual machine (VM) running on a host "cloud" server system 2024 and executing instructions retrieved from a connected memory (not shown). In certain embodiments, the server 2020 stores the encrypted file 2014 in a connected database 2022. In certain embodiments, the server 2020 provides only information related to the file transfer, e.g., an acknowledgement of a successful upload. In certain embodiments, the encrypted file 2014 is erased from the non-volatile memory of the analyzer 2010 after a successful upload. In certain embodiments, a copy of the encrypted file 2014 can be transferred from the database 2022 to other storage devices, e.g., a backup database 2030 or a customer database 2032. In certain embodiments, the file 2014 remains encrypted on all databased, e.g., 2022, 2030, and 2032, and inaccessible, e.g., by a customer or $3^{rd}$ party, outside the server 2020.

The system database 2022 includes algorithms, parameters, and libraries. In certain embodiments, the algorithms, parameters, and libraries are encrypted in the database 2022 and are never shared in unencrypted form outside the secure server system 2024. To analyze a data record 2012, the relevant encrypted file 2014 and necessary encrypted algorithm, parameters, and library are loaded into the server 2020. The server 2020 also retrieves the one or more keys required to decrypt the various files. The server 2020 then decrypts the various files, analyzes the measurements, and produces one or more results, e.g., a percentage value of a material in the sample. The results are saved in a results record on the database 2022. In certain embodiments, the results record is encrypted with a different key, e.g., a key unique to a customer associated with the holder identifier such that the customer will be able to decrypt the results record and view the results.

In certain embodiments, customers can retrieve and store copies of their encrypted files 2014 in any manner. In combination with physical archiving of the original sample 2050 in the holder 2060, this enables repeated analysis and trending, e.g., study of the effect of aging on the sample 2050.

In certain embodiments, the encryption keys required to analyze the measurements are retained within secure systems, e.g., the cloud-based server system 2024. In certain embodiments, the algorithms, parameters, and libraries are stored in encrypted form and decrypted only when in use by the server and then saved only in volatile memory.

Figure 21:
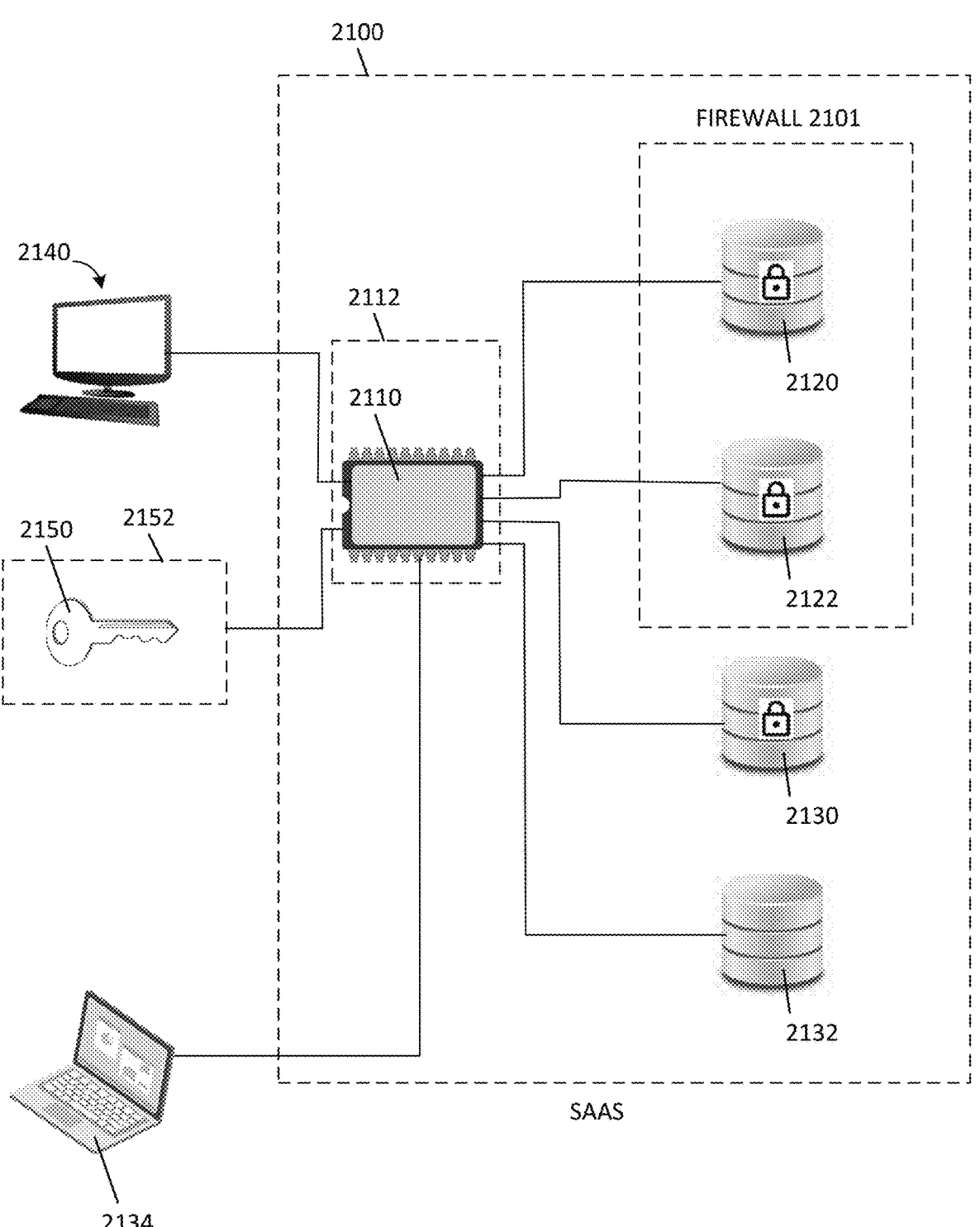
FIG. 21 is a block diagram of an exemplary analysis system, according to certain aspects of the present disclosure.

FIG. 21 is a block diagram of an exemplary analysis system 2100, according to certain aspects of the present disclosure. In this example, the system 2100 is implemented as a cloud-hosted Software As A Service (SAAS), e.g., hosted by an on-demand cloud computing platform. The system 2100 comprises a processor 2110 running on a VM 2112 that is connected to various databases 2120, 2122, 2130, 2132. In certain embodiments, an administrator can access the processor 2110 through a proprietary interface from a remote computer 2140. Other methods of hosting a software service and providing administrative management, as known to those of skill in the art, are included in this disclosure.

In certain embodiments, there is an algorithm database 2120 that stores encrypted algorithms that are used to analyze the measurements made by the analyzer. In certain embodiments, there is a library database 2122 that stores encrypted representations of known spectral patterns associated with specific materials. In certain embodiments, there is a customer record database 2130 that stores customers' files, e.g., encrypted data record files, e.g., file 2014 from FIG. 20, and results files.

In certain embodiments, there is a "paid services" database 2132 that stores records of what analytical services have been ordered and/or paid for by the customer for each holder 2060. In certain embodiments, the purchase price of a holder 2060 includes a basic service, e.g., determination of a concentration of a single pre-determined material. In certain embodiments, a customer may order an additional analysis of one or more samples 2050, whereupon the encrypted files associated with the holders 2060 containing the samples 2050 are retrieved, the data records 2012 extracted, the additional algorithms and libraries retrieved and decrypted, and the additional analysis performed. A new results record is created, saved, and provided to the customer.

In certain embodiments, the algorithm and library databases 2120, 2122 are further sequestered behind a firewall 2101 to prevent the algorithms and libraries from becoming known. It is advantageous to retain all algorithms, parameters, and libraries within a secure environment so as to avoid unauthorized duplication or reverse-engineering of this critical knowledge.

In the example of FIG. 21, a single key is used to decrypt all of the files in the system. In certain embodiments, this key 2150 is stored separately from the SAAS host 2100, e.g., on a secure computer 2152 located at a physically separate location. In certain embodiments, the processor 2110 connects to the secure computer 2152, e.g., via a virtual private network (VPN), and retrieves the key 2150 when needed to process data records. In certain embodiments, the key 2150 is never saved in non-volatile memory in the SAAS. In certain embodiments, the key 2150 is securely stored within the SAAS 2100 and an administrator must provide information, e.g., a password, to the processor 2110 to enable access to the stored password. In certain embodiments, the key 2150 is stored on a separate physical device, e.g., a dongle (not shown in FIG. 21), that must be connected to enable the processor 2110 to retrieve the key 2150.

In certain embodiments, results are encrypted using a customer-unique key such that the customer may decrypt the results record but all others are unable to do so.

In certain embodiments, a customer may access the processor 2110 directly, e.g., through a public portal using a standard browser 2134. In certain embodiments, the customer may request services, e.g., a new analysis of a stored data record, order material such as additional new sample holders, or upload encrypted files for analysis.

In summary, the disclosed secure analysis system includes a portable analyzer that can be taken to a field where samples of plants are collected, loaded into a sample holder, and analyzed on the spot. The analyzer creates encrypted files that contain the measurements and information related to the holder and the analysis event. The encrypted file is uploaded to a cloud-based server where the measurements are analyzed. As the decryption capability is available only within the secure SAAS system, the algorithms, parameter, and libraries remain proprietary.

Embodiments

A1. An apparatus for analysis of a sample, comprising: a frame having a first axis; a sample holder coupled to the frame and disposed on the first axis; a transmissive diffraction grating coupled to the frame and disposed along the first axis such that light traveling along the first axis from the sample holder passes through the grating in a first direction; and a source coupled to the frame and configured to emit a first light to pass through the grating in a second direction that is opposite the first direction.

A2. The apparatus of A1, further comprising: a lens coupled to the frame; and a spatial filter coupled to the frame; wherein the lens and spatial filter are disposed along the first optical axis.

A3. The apparatus of A1, wherein a portion of the first light emitted by the source is diffracted by the grating to travel parallel to the first optical axis.

A4. The apparatus of A3, wherein: the light emitted by the source is monochromatic; the diffracted portion of the first light comprises a mode; the light emitted by the source travels to the grating along a second optical axis that is not parallel to the first optical axis; and an angle between the first and second optical axes determines the mode of the diffracted portion of the first light.

A5. The apparatus of A4, wherein: the light source comprises a plurality of sources each emitting light at a plurality of unique frequencies; the second optical axis comprises a plurality of secondary optical axes that are respectively associated with the plurality of unique frequencies and respectively disposed at a plurality of unique angles to the first optical axis.

A6. The apparatus of A3, wherein: the light emitted by the source is white light; the diffracted portion of the white light comprises a color; the light emitted by the source travels to the grating along a second optical axis that is not parallel to the first optical axis; and an angle between the first and second optical axes determines the color of the diffracted portion of the light.

A7. The apparatus of A1, wherein: the sample holder is configured to accept the sample such that the sample is disposed on the first optical axis; the first light illuminates the sample, whereupon the sample emits a second light that enters the grating in the first direction; and a portion of the second light exits the grating as diffracted second light; the apparatus further comprises: a lens coupled to the frame and configured to focus the diffracted second light to form a Raman spectrum; a detector coupled to the frame and configured to sense the Raman spectrum and provide data related to the Raman spectrum; a processor communicatively coupled to the detector; and a non-volatile memory communicatively coupled to the processor and comprising: a reference file associated with a material; and an instruction file that, when executed by the processor, causes the processor to receive the data from the detector, compare the received data with a portion of the reference file, and determine an attribute of the sample.

A8. The apparatus of A7, wherein the attribute of the sample comprises an amount of a material component in the sample.

A9. The apparatus of A1, wherein the light passes from the source to the grating without being reflected.

B1. A method of obtaining a Raman spectrum of a sample, the method comprising the steps of: illuminating the sample with a first light, whereupon the sample emits a second light that passes through a transmissive diffraction grating in a first direction and exits the grating as diffracted second light, wherein the first light passed through the grating in a second direction opposite the first direction prior to illuminating the sample; focusing the diffracted second light to form a Raman spectrum.

B2. The method of B1, further comprising the steps of: coupling a disposable element to an apparatus, wherein the disposable element comprises a sample holder and the grating and the apparatus comprises a light source configured to emit the first light; and placing the sample on the sample holder.

B3. The method of B1, wherein the first light is coherent.

B4. The method of B1, wherein the first light is monochromatic.

B5. The method of B1, further comprising the step of filtering the second light to remove a portion of the first light.

B6. The method of B1, further comprising the step of evaluating the Raman spectra to determine an attribute of the sample.

B7. The method of B6, wherein the attribute of the sample comprises an amount of a material component in the sample.

C1. An apparatus for analysis of a sample of a material, comprising a holder configured to accept the sample, the holder comprising a sample plate comprising a first surface configured to contact the accepted sample; and a sample lens array coupled to the sample plate, the sample lens array comprising a plurality of focusing elements.

C2. The apparatus of C1, wherein the holder further comprises a slit array coupled to the sample lens array, the slit array comprising a plurality of slits; and a collimating lens array coupled to the slit array, the collimating lens array comprising a plurality of collimating lenses.

C3. The apparatus of C1, wherein the plurality of focusing elements are configured to collect light from a respective plurality of regions of the surface of the sample and produce a respective plurality of beams of light.

C4. The apparatus of C2, wherein a portion of the plurality of focusing elements are arranged in a first straight row that is parallel to a first slit of the plurality of slits of the slit array; and the focusing elements of the first row are configured to focus their respective beams of light on the first slit.

C5. The apparatus of C4, wherein the plurality of collimating lenses are configured to receive a portion of the plurality of beams of light that pass through the plurality of slits; and modify each of the plurality of beams of light such that all of the modified plurality of beams of light are collimated in a common direction.

C6. The apparatus of C1, wherein the holder further comprises a compartment configured to accept the sample, wherein the sample plate forms a portion of the compartment; and a lid that is coupled to the holder and configured to selectably close over the compartment and permanently prevent removal of an accepted sample from the holder.

C7. The apparatus of C1, wherein the focusing elements are holographic lenses.

C8. The apparatus of C2, wherein the collimating lenses are holographic lenses.

C9. The apparatus of C1, wherein the sample plate further comprises a channel configured to accept a liquid sample.

C10. The apparatus of C1, wherein the sample plate further comprises an actuator selected from the group of a temperature control element, a filtering element, and a stimulation element.

C11. The apparatus of C1, wherein the holder is configured to accept a beam of illuminating light and guide the accepted beam of illuminating light to a side of the sample plate that is not the first surface.

C12. The apparatus of C1, further comprising a frame configured to removably accept the holder; a detector coupled to the frame; a focusing lens coupled to the frame; and a transmissive diffraction grating coupled to the frame.

C13. The apparatus of C12, further comprising an optical filter coupled to the frame; and a spatial filter coupled to the frame.

C14. The apparatus of C12, wherein the grating comprises a first surface and a second surface that is opposite the first surface; a portion of a beam of light emitted by the accepted sample passes through the grating from the first surface to the second surface; and the frame is further configured to accept a beam of illuminating light and guide the accepted beam of illuminating light to the second surface of the grating such that a refracted portion of the beam of illuminating light is directed through the grating and exits the first surface toward the accepted sample.

C15. The apparatus of C1, wherein the holder is configured for use with only a single sample.

Headings and subheadings, if any, are used for convenience only and do not limit the invention.

Reference to an element in the singular is not intended to mean "one and only one" unless specifically so stated, but rather "one or more." Use of the articles "a" and "an" is to be interpreted as equivalent to the phrase "at least one." Unless specifically stated otherwise, the terms "a set" and "some" refer to one or more.

Terms such as "top," "bottom," "upper," "lower," "left," "right," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Although the relationships among various components are described herein and/or are illustrated as being orthogonal or perpendicular, those components can be arranged in other configurations in some embodiments. For example, the angles formed between the referenced components can be greater or less than 90 degrees in some embodiments.

Although various components are illustrated as being flat and/or straight, those components can have other configurations, such as curved or tapered for example, in some embodiments.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "operation for."

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such as an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A system for analyzing a sample, comprising:
a sample holder comprising:
    a body comprising a unique holder identifier that is uniquely associated with the sample holder;
    a sample compartment formed in the body and configured to contain the sample;
    a cap configured to attach to the body and seal the sample compartment; and
    a tamper-evident feature that provides residual physical evidence when the sample compartment has been accessed after the cap is sealed to the body;
an analyzer configured to retrieve the unique holder identifier from the sample holder and:
    create a measurement of the sample contained in the sample compartment;
    create a data record of the measurement;

encrypt the data record and a portion of the retrieved unique holder identifier and an authentication parameter to form an encrypted file; and
    provide the encrypted file; and
a server communicatively coupled to the analyzer and configured to:
    receive the encrypted file;
    retrieve an encryption key;
    decrypt the encrypted file using the encryption key;
    analyze the measurement; and
    provide a result that is based in part on the analysis of the measurement and comprises the portion of the unique holder identifier;
    wherein the combination of the tamper-evident feature and the unique holder identifier of the holder, the inclusion of the portion of the unique holder identifier in the encrypted file, the authentication parameter of the encrypted file, and the inclusion of the portion of the unique holder identifier in the result provide chain-of-custody evidence that the result is associated with the sample contained in the sample holder.

2. The system of claim 1, wherein the analyzer is further configured to store the measurement and the data record only in a volatile memory.

3. The system of claim 1, wherein the analyzer is further configured to erase the measurement and the data record after the encrypted file is formed.

4. The system of claim 1, wherein:
the encrypted file comprises one or more of a date, a time, a location, information entered by the user, information determined by the analyzer, and a user identifier that are associated with the measurement.

5. A method of providing chain-of-custody evidence that a result of analyzing a sample is associated with the analyzed sample, comprising steps:
    loading the sample into a sample compartment of a sample holder that comprises a unique holder identifier that is uniquely associated with the sample holder;
    sealing the sample compartment with a cap that comprises a tamper-evident feature that provides residual physical evidence when the sample compartment has been accessed after the cap is attached to the body;
    creating a measurement of the sample;
    creating a data record of the measurement;
    retrieving the unique holder identifier from the sample holder;
    encrypting the data record and an authentication parameter and a portion of the retrieved unique holder identifier to form an encrypted file;
    decrypting the encrypted file;
    analyzing the measurement; and
    providing a result that is based in part on the analysis of the measurement and comprises the portion of the unique holder identifier;
    wherein the combination of the tamper-evident feature and the unique holder identifier of the holder, the inclusion of the portion of the unique holder identifier in the encrypted file, the authentication parameter of the encrypted file, and the inclusion of the portion of the unique holder identifier in the result provide chain-of-custody evidence that the result is associated with the sample contained in the sample holder.

6. The method of claim 5, wherein the measurement and the data record are stored only in a volatile memory.

7. The method of claim 5, further comprising the step:
    erasing, after the encrypted file is formed, the data record.

8. The method of claim 5, wherein the encrypted file comprises one or more of a date, a time, a location, information entered by the user, information determined by the analyzer, and a user identifier that are associated with the measurement.

* * * * *